US009006390B2

(12) United States Patent
Bachinsky et al.

(10) Patent No.: US 9,006,390 B2
(45) Date of Patent: Apr. 14, 2015

(54) MEK LIGANDS AND POLYNUCLEOTIDES ENCODING MEK LIGANDS

(71) Applicant: Intrexon Corporation, Blacksburg, VA (US)

(72) Inventors: David Bachinsky, Blacksburg, VA (US); Jonathan Carson, Blacksburg, VA (US); Amy Atzel, Minneapolis, MN (US); Thomas Reed, Arlington, VA (US)

(73) Assignee: Intrexon Corporation, Blacksburg, VA (US)

(*) Notice: Subject to any disclaimer, the term of this patent is extended or adjusted under 35 U.S.C. 154(b) by 0 days.

(21) Appl. No.: 14/046,454

(22) Filed: Oct. 4, 2013

(65) Prior Publication Data
US 2014/0073028 A1 Mar. 13, 2014

Related U.S. Application Data

(63) Continuation of application No. 12/532,912, filed as application No. PCT/US2008/058531 on Mar. 27, 2008, now Pat. No. 8,575,304.

(60) Provisional application No. 60/908,231, filed on Mar. 27, 2007.

(51) Int. Cl.
*A61K 38/00* (2006.01)
*C07K 4/00* (2006.01)
*C07K 7/00* (2006.01)
*C07K 14/00* (2006.01)
*C07K 14/47* (2006.01)
*C12N 9/12* (2006.01)

(52) U.S. Cl.
CPC ......... *C07K 14/4703* (2013.01); *C07K 2319/00* (2013.01); *C12N 9/1205* (2013.01); *C12Y 207/11024* (2013.01); *C12Y 207/12002* (2013.01)

(58) Field of Classification Search
USPC .......................... 530/300, 324, 326, 327, 350
See application file for complete search history.

(56) References Cited

U.S. PATENT DOCUMENTS

| | | | |
|---|---|---|---|
| 7,071,295 | B2 | 7/2006 | Reed |
| 8,575,304 | B2 | 11/2013 | Reed et al. |
| 2003/0224500 | A1 | 12/2003 | Ohren et al. |
| 2004/0185556 | A1 | 9/2004 | Reed |
| 2005/0089932 | A1 | 4/2005 | Kolkman et al. |
| 2005/0214755 | A1* | 9/2005 | Agrez et al. ............. 435/6 |
| 2008/0032947 | A1 | 2/2008 | Reed |
| 2008/0050808 | A1 | 2/2008 | Reed et al. |
| 2008/0051360 | A1 | 2/2008 | Reed et al. |
| 2008/0213834 | A1 | 9/2008 | Reed et al. |
| 2008/0220475 | A1 | 9/2008 | Reed et al. |
| 2009/0186379 | A1 | 7/2009 | Reed |
| 2009/0215173 | A1 | 8/2009 | Reed |
| 2009/0215866 | A1 | 8/2009 | Reed |

FOREIGN PATENT DOCUMENTS

| | | | |
|---|---|---|---|
| WO | WO 00/50901 | 8/2000 | |
| WO | WO 02/051993 A1 | 7/2002 | |
| WO | WO 2004/001008 | 12/2003 | |
| WO | WO 2005/040336 A2 | 5/2005 | |
| WO | WO 2005/113812 | 12/2005 | |
| WO | WO 2005/116231 A1 | 12/2005 | |
| WO | WO 2006/039367 * | 4/2006 | ........... C07K 14/435 |
| WO | WO 2007/008917 A2 | 1/2007 | |
| WO | WO 2007/048103 A2 | 4/2007 | |
| WO | WO 2007/076166 A2 | 7/2007 | |
| WO | WO 2008/119058 A2 | 10/2008 | |
| WO | WO 2008/119058 A3 | 10/2008 | |

OTHER PUBLICATIONS

Abe et al., "Extracellular Signal-Regulated Kinase 7 (ERK7), a Novel ERK with a C-Terminal Domain That Regulates Its Activity, Its Cellular Localization, and Cell Growth," *Molecular and Cellular Biology* 19: 1301-1312, American Society for Microbiology, (1999).
Cobb, M.H., "MAP kinase pathways," *Progress in Biophysics & Molecular Biology* 71: 479-500, Pergamon Press (1999).
Janssen et al., "Ras- and Raf-Induced Down-modulation of Non-muscle Tropomyosin Are MEK-Independent," *J. Biol. Chemistry* 273: 32182-32186, The American Society for Biochemistry and Molecular Biology, Inc. (1998).
Ji, Y., et al., "Targeted Inhibition of $Ca^{2+}$/Calmodulin-dependent Protein Kinase II in Cardiac Longitudinal Sarcoplasmic Reticulum Results in Decreased Phospholamban Phosphorylation at Threonine 17," *J. Biol. Chem.* 278:25063-25071, The American Society for Biochemistry and Molecular Biology, Inc. (2003).
Kostich et al., "Human members of the eukaryotic protein kinase family," *Genome Biology* 3: 1-12, BioMed Central Ltd. (2002).
Robinson et al., "A constitutively active and nuclear form of the MAP kinase ERK2 is sufficient for neurite outgrowth and cell transformation," *Current Biology* 8: 1141-1150, Current Biology Ltd. (1998).
Schaeffer et al., "MP1: A MEK Binding Partner That Enhances Enzymatic Activation of the MAP Kinas Cascade," *Science* 281: 1668-1671, American Association for the Advancement of Science (1998).
Wriggers et al., "Control of Protein Functional Dynamics by Peptide Linkers," *Biopolymers* 80: 736-746, Wiley Interscience (2005).
Written Opinion of the International Searching Authority in Application No. PCT/US2008/058531, inventors Bachinsky et al. (Dec. 8, 2008).

(Continued)

*Primary Examiner* — Amber D Steele
(74) *Attorney, Agent, or Firm* — Sterne, Kessler, Goldstein & Fox P.L.L.C.

(57) ABSTRACT

The invention relates to kinase ligands and polyligands. In particular, the invention relates to ligands, homopolyligands, and heteropolyligands that modulate MEK activity. The ligands and polyligands are utilized as research tools or as therapeutics. The invention includes linkage of the ligands, homopolyligands, and heteropolyligands to a cellular localization signal, epitope tag and/or a reporter. The invention also includes polynucleotides encoding the ligands and polyligands.

17 Claims, 27 Drawing Sheets

(56) References Cited

OTHER PUBLICATIONS

International Preliminary Report on Patentability in Application No. PCT/US2008/058531, inventors Bachinsky et al. (Sep. 29, 2009).

UniProtKB/TrEMBL Accession No. O35558, "Mapk1/ERK2," downloaded from http://www.uniprot.org/uniprot/O35558, and printed on Jul. 19, 2010, 5 pages.

UniProtKB/TrEMBL Accession No. Q7Z3H5, "Putative uncharacterized protein DKFZp686O0215," downloaded from http://www.uniprot.org/uniprot/Q7Z3H5.html, and printed on Jul. 19, 2010, 4 pages.

Catling, A.D. et al., "A Proline-Rich Sequence Unique to MEK1 and MEK2 is Required for Raf Binding and Regulates MEK Function," *Mol. Cell. Biol.* 15: 5214-5225, American Society for Microbiology, Washington, D.C., U.S.A. (1995).

Engelman, J. et al., "Caveolin-mediated regulation of signaling along the p42/44 MAP kinase cascade in vivo—A role for the caveolin-scaffolding domain," *FEBS Letters* 428: 205-211, Elsevier, Amsterdam, NL (1998).

Tokmakov, A.A. et al., "Inhibition of MAPK Pathway by a Synthetic Peptide Corresponding to the Activation Segment of MAPK," *Biochem. Biophys. Res. Comm.* 252: 214-219, Academic Press, Orlando, FL., U.S.A. (1998).

Frost, J. et al., "Cross-cascade activation of ERKs and ternary complex factors by Rho family proteins," *EMBO Journal* 16: 6426-6438, Oxford University Press, Surrey, GB (1997).

Office Action mailed Aug. 23, 2012 in U.S. Appl. No. 12/532,912, filed Mar. 22, 2010, inventors Bachinsky, D. et al.

Office Action mailed Feb. 1, 2013 in U.S. Appl. No. 12/532,912, filed Mar. 22, 2010, inventors Bachinsky, D. et al.

* cited by examiner

| LIGAND X | LIGAND Y |
|---|---|

FIGURE 3A

| LIGAND X | LIGAND Y | LIGAND Z |
|---|---|---|

FIGURE 3B

| LIGAND X | LIGAND Y | LIGAND X | LIGAND Z | LIGAND A |
|---|---|---|---|---|

FIGURE 3C

| LIGAND A | LIGAND B | LIGAND C | LIGAND D |
|---|---|---|---|

FIGURE 3D

| LIGAND A | LIGAND A | LIGAND B | LIGAND C |
|---|---|---|---|

FIGURE 3E

| LIGAND B | SPACER | LIGAND A |

FIGURE 4A

| LIGAND Z | SPACER | LIGAND Y | SPACER | LIGAND X |

FIGURE 4B

| LIGAND A | SPACER | LIGAND B | SPACER | LIGAND A | SPACER | LIGAND B |

FIGURE 4C

| LIGAND A | SPACER | LIGAND B | SPACER | LIGAND C | SPACER | LIGAND D |

FIGURE 4D

| LIGAND X | SPACER | LIGAND Y | SPACER | LIGAND X | SPACER | LIGAND Y | SPACER | LIGAND Z |

FIGURE 4E

| LIGAND C | SPACER | LIGAND Y | SPACER | LIGAND Z | SPACER | LIGAND Y |

FIGURE 4F

| LIGAND A | LIGAND B | LIGAND C | LIGAND D | EPITOPE | LOCALIZATION SIGNAL |

FIGURE 8A

| LOCALIZATION SIGNAL | LIGAND X | LIGAND Y | EPITOPE |

FIGURE 8B

| EPITOPE | LIGAND X | SPACER | LIGAND X | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | LIGAND Z | SPACER | LIGAND Y | LIGAND B | EPITOPE |

FIGURE 8F

| EPITOPE | LIGAND B | LOCALIZATION SIGNAL |

FIGURE 8G

| PROMOTER | LIGAND or POLYLIGAND | EPITOPE | LOCALIZATION SIGNAL | STOP | POLY-A |

FIGURE 9A

| PROMOTER | OPTIONAL REPORTER | OPTIONAL EPITOPE | LIGAND or POLYLIGAND | OPTIONAL LOCALIZATION SIGNAL | STOP | POLY-A |

FIGURE 9B

| PROMOTER | LIGAND or POLYLIGAND | REPORTER | LOCALIZATION SIGNAL | STOP | POLY-A |

FIGURE 9C

| PROMOTER | LIGAND or POLYLIGAND | OPTIONAL EPITOPE | OPTIONAL REPORTER | OPTIONAL LOCALIZATION SIGNAL | STOP | POLY-A |

FIGURE 9D

| PROMOTER | LIGAND or POLYLIGAND | LOCALIZATION SIGNAL | STOP | POLY-A |

FIGURE 9E

| PROMOTER | LOCALIZATION SIGNAL | LIGAND or POLYLIGAND | STOP | POLY-A |

FIGURE 9F

| PROMOTER | LIGAND or POLYLIGAND | STOP | POLY-A |

FIGURE 9G

VVN-40637 CMV UTR-1 Kozak MEK1 LacZ hGHpA in VVN-3836

VVN-40639 CMV UTR-1 Kozak Legacy-MEK-Dcy-45-1 LacZ hGHpA in VVN-3836

VVN-40641 CMV UTR-1 Kozak Legacy-MEK-Dcy-45-2 LacZ hGHpA in VVN-3836

VVN-40643 CMV UTR-1 Kozak Legacy-MEK-Dcy-45-3 LacZ hGHpA in VVN-3836

VVN-40645 CMV UTR-1 Kozak Legacy-MEK-Dcy-45-4 LacZ hGHpA in VVN-3836

VVN-40647 CMV UTR-1 Kozak Legacy-MEK-Dcy-45-5 LacZ hGHpA in VVN-3836

VVN-40649 CMV UTR-1 Kozak Legacy-MEK-Dcy-45-6 LacZ hGHpA in VVN-3836

VVN-40650 UTR-1 Legacy-MEK-Dcy-45-7 LacZ in VVN-3688

VVN-40651 CMV UTR-1 Kozak Legacy-MEK-Dcy-45-7 LacZ hGHpA in VVN-3836

VVN-40652 UTR-1 Legacy-MEK-Dcy-45-8 LacZ in VVN-3688

VVN-40653 CMV UTR-1 Kozak Legacy-MEK-Dcy-45-8 LacZ hGHpA in VVN-3836

VVN-40654 UTR-1 Legacy-MEK-Dcy-45-9 LacZ in VVN-3688

VVN-40655 CMV UTR-1 Kozak Legacy-MEK-Dcy-45-9 LacZ hGHpA in VVN-3836

| VECTOR USED FOR TRANSFECTION (VECTOR #) | VECTOR FIGURE # | LIGAND DESIGNATION | LIGAND SEQ ID NO: | AVERAGE CONCENTRATION OF LIGAND FUSION PROTEIN IN LYSATE (ng/ml) | STD DEV |
|---|---|---|---|---|---|
| VVN-40637 | 12 | Similar to 45-9 | 33 | 50.16 | 6.65 |
| VVN-40639 | 13 | MEK-DCY-45-1 | 1 | 8.79 | 0.39 |
| VVN-40641 | 14 | MEK-DCY-45-2 | 5 | 9.80 | 0.45 |
| VVN-40643 | 15 | MEK-DCY-45-3 | 9 | 25.34 | 0.95 |
| VVN-40645 | 16 | MEK-DCY-45-4 | 13 | 5.14 | 0.16 |
| VVN-40647* | 17 | MEK-DCY-45-5 | 17 | 32.03 | N/A |
| VVN-40649 | 18 | MEK-DCY-45-6 | 21 | 28.57 | 2.29 |
| VVN-40651 | 20 | MEK-DCY-45-7 | 25 | 43.10 | 3.24 |
| VVN-40653 | 22 | MEK-DCY-45-8 | 29 | 36.26 | 3.42 |
| VVN-40655 | 24 | MEK-DCY-45-9 | 33 | 183.81 | 32.29 |
| ERK Positive Control | N/A | ERK1 + con | 38 | 213.10 | 55.99 |

* VVN-40647 data represents the value of 1 replicate (other replicate was below limit of detection)

MEK LIGANDS AND POLYNUCLEOTIDES ENCODING MEK LIGANDS

REFERENCE TO SEQUENCE LISTING SUBMITTED ELECTRONICALLY VIA EFS-WEB

This application includes a "Sequence_Listing.ascii.txt," 46,806 bytes, created on Oct. 4, 2013, and submitted electronically via EFS-Web, which is hereby incorporated by reference in its entirety.

FIELD OF INVENTION

The invention relates to mammalian kinase ligands, substrates and modulators. In particular, the invention relates to polypeptides, polypeptide compositions and polynucleotides that encode polypeptides that are ligands, substrates, and/or modulators of MEK. The invention also relates to polyligands that are homopolyligands or heteropolyligands that modulate MEK activity. The invention also relates to ligands and polyligands localized to a subcellular region.

Application Ser. No. 12/532,912 (now U.S. Pat. No. 8,575, 304), application Ser. No. 10/724,532 (now U.S. Pat. No. 7,071,295), application Ser. No. 10/682,764 (US2004/0185556, PCT/US2004/013517, WO2005/040336), application Ser. No. 11/233,246, and US20040572011P (WO2005116231). Each of these patents and applications is are hereby incorporated by reference.

BACKGROUND AND PRIOR ART

Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Phosphatases are enzymes that remove phosphate from a molecule. The removal of phosphate is called dephosphorylation. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

MAP/ERK kinase 1, MEK1, PRKMK1, MAPKK1, MAP2K1, MKK1 are the same enzyme, known as MEK1. MAP/ERK kinase 2, MEK2, PRKMK2, MAPKK2, MAP2K2, MKK2 are the same enzyme, known as MEK2. MEK1 and MEK2 can phosphorylate serine, threonine and tyrosine residues in protein or peptide substrates. To date, few cellular substrates of MEK isoforms have been identified. While individual substrates or ligands have been identified and studied, mixed ligands linked together as polyligands that modulate MEK isoform activity have not been demonstrated before this invention.

Design and synthesis of polypeptide ligands that modulate calcium/calmodulin-dependent protein kinase and that localize to the cardiac sarco(endo)plasmic reticulum was performed by Ji et al. (J Biol Chem (2003) 278:25063-71). Ji et al. accomplished this by generating expression constructs that localized calcium/calmodulin-dependent protein kinase inhibitory polypeptide ligands to the sarcoplasmic reticulum by fusing a sarcoplasmic reticulum localization signal derived from phospholamban to a polypeptide ligand. See also U.S. Pat. No. 7,071,295.

Detailed Description of Polypeptide and Polynucleotide Sequences

SEQ ID NOS:1-36 are example polyligands and polynucleotides encoding them.

Specifically, the MEK polyligand of SEQ ID NO:1 is encoded by SEQ ID NO:2, SEQ ID NO:3, and SEQ ID NO:4, wherein the codons have been optimized for mammalian expression and vector insertion, and wherein SEQ ID NOS: 3-4 contain alternative flanking restriction sites applicable to modular cloning methods. SEQ ID NO:1 is an embodiment of a polyligand of the structure A-S1-B-S2-C-S3-D, wherein A is SEQ ID NO:41, B is SEQ ID NO:42, C is SEQ ID NO:49, and D is SEQ ID NO:43, wherein Xaa is alanine or phenylalanine, and wherein S1 is a spacer of the amino acid sequence PGAAG (SEQ ID NO: 52), and S2 is a spacer of amino acid sequence PAGGA (SEQ ID NO: 54), and S3 is a spacer of the amino acid sequence PGAAG (SEQ ID NO: 52). A polyligand of structure A-S1-B-S2-C-S3-D is also called herein a heteropolyligand, shown generically in FIG. 4D.

SEQ ID NO:5 is an embodiment of a polyligand of the structure X-S1-X-S2-Y-S3-Z, wherein X is SEQ ID NO:44, Y is SEQ ID NO:42, Z is SEQ ID NO:43, wherein Xaa is alanine or phenylalanine, and wherein S1 is a spacer of amino acid sequence PGAAG (SEQ ID NO: 52), S2 is a spacer of the amino acid sequence PAGGA (SEQ ID NO: 54), and S3 is a spacer of the amino acid sequence PGAAG (SEQ ID NO: 52). The MEK polyligand of SEQ ID NO:5 is encoded by SEQ ID NO:6, SEQ ID NO:7 and by SEQ ID NO:8, wherein the codons have been optimized for mammalian expression and vector insertion, and wherein SEQ ID NOS:7-8 contain alternative flanking restriction sites applicable to modular cloning methods. A polyligand of structure X-S1-X-S2-Y-S3-Z is also called herein a heteropolyligand, shown generically in FIG. 4E.

SEQ ID NO:9 is encoded by SEQ ID NO:10, SEQ ID NO:11, and SEQ ID NO:12, wherein the codons have been optimized for mammalian expression and vector insertion, and wherein SEQ ID NOS:11-12 contain alternative flanking restriction sites applicable to modular cloning methods. SEQ ID NO:1 is an embodiment of a polyligand of the structure A-S1-B-S2-C-S3-D, wherein A is SEQ ID NO:41, B is SEQ ID NO:42, C is SEQ ID NO:49, and D is SEQ ID NO:43, wherein Xaa is serine, threonine or tyrosine, and wherein S1 is a spacer of the amino acid sequence PGAAG (SEQ ID NO: 52), and S2 is a spacer of amino acid sequence PAGGA (SEQ ID NO: 54), and S3 is a spacer of the amino acid sequence PGAAG (SEQ ID NO: 52). A polyligand of structure A-S1-B-S2-C-S3-D is also called herein a heteropolyligand, shown generically in FIG. 4D.

SEQ ID NO:13 is an embodiment of a polyligand of the structure X-S1-X-S2-Y-S3-Z, wherein X is SEQ ID NO:44, Y is SEQ ID NO:42, Z is SEQ ID NO:43, wherein Xaa is serine, threonine or 10 tyrosine, and wherein Si is a spacer of amino acid sequence PGAAG (SEQ ID NO: 52), S2 is a spacer of the amino acid sequence PAGGA (SEQ ID NO: 54), and S3 is a spacer of the amino acid sequence PGAAG (SEQ ID NO: 52). The MEK polyligand of SEQ ID NO:13 is encoded by SEQ ID NO:14, SEQ ID NO:15 and by SEQ ID NO:16, wherein the codons have been optimized for mammalian expression and vector insertion, and wherein SEQ ID NOS:15-16 contain alternative flanking restriction sites applicable to modular cloning methods. A polyligand of structure X-S11-X-S2-Y-S3-Z is also called herein a heteropolyligand, shown generically in FIG. 4E.

SEQ ID NO:17 is encoded by SEQ ID NO:18, SEQ ID NO:19, and SEQ ID NO:20, wherein the codons have been optimized for mammalian expression and vector insertion, and wherein SEQ ID NOS:19-20 contain alternative flanking restriction sites applicable to modular cloning methods. SEQ ID NO:17 is an embodiment of a polyligand of the structure A-S1-B-S2-C-S3-D, wherein A is SEQ ID NO:51, B is SEQ ID NO:43, C is SEQ ID NO:42, and D is SEQ ID NO:44, wherein Xaa is alanine or phenylalanine, and wherein S1 is a spacer of the amino acid sequence PGAAG (SEQ ID NO: 52), and S2 is a spacer of amino acid sequence PAGGA (SEQ ID NO: 54), and S3 is a spacer of the amino acid sequence PGAAG (SEQ ID NO: 52). A polyligand of structure A-S1-B-S2-C-S3-D is also called herein a heteropolyligand, shown generically in FIG. 4D.

SEQ ID NO:21 is encoded by SEQ ID NO:22, SEQ ID NO:23, and SEQ ID NO:24, wherein the codons have been optimized for mammalian expression and vector insertion, and wherein SEQ ID NOS:23-24 contain alternative flanking restriction sites applicable to modular cloning methods. SEQ ID NO:21 is an embodiment of a polyligand of the structure A-S1-A-S2-A, wherein A is SEQ ID NO:45, wherein Xaa is alanine or phenylalanine, and wherein S1 is a spacer of the amino acid sequence PGAAG (SEQ ID NO: 52), and S2 is a spacer of amino acid sequence PAGGA (SEQ ID NO: 54), and S3 is a spacer of the amino acid sequence PGAAG (SEQ ID NO: 52). A polyligand of structure A-S1-A-S2-A is also called herein a homopolyligand, shown generically in FIG. 2D.

SEQ ID NO:25 is encoded by SEQ ID NO:26, SEQ ID NO:27, and SEQ ID NO:28, wherein the codons have been optimized for mammalian expression and vector insertion, and wherein SEQ ID NOS:27-28 contain alternative flanking restriction sites applicable to modular cloning methods. SEQ ID NO:25 is an embodiment of a monomeric ligand, wherein Xaa is alanine or phenylalanine.

SEQ ID NO:29 is encoded by SEQ ID NO:30, SEQ ID NO:31, and SEQ ID NO:32, wherein the codons have been optimized for mammalian expression and vector insertion, and wherein SEQ ID NOS:31-32 contain alternative flanking restriction sites applicable to modular cloning methods. SEQ ID NO:29 is an embodiment of a monomeric ligand, wherein Xaa is alanine.

SEQ ID NO:33 is encoded by SEQ ID NO:34, SEQ ID NO:35, and SEQ ID NO:36, wherein the codons have been optimized for mammalian expression and vector insertion, and wherein SEQ ID NOS:35-36 contain alternative flanking restriction sites applicable to modular cloning methods. SEQ ID NO:33 is an embodiment of a polyligand of the structure A-S4-B-S5-A-S4-B, wherein A is SEQ ID NO:48, B is SEQ ID NO:50, wherein Xaa is alanine, and wherein S4 is a spacer of the amino acid sequence RRPAAA (SEQ ID NO: 53), and S5 is a spacer of amino acid sequence PGGG (SEQ ID NO: 55). A polyligand of structure A-S4B-S5-A-S4-B is also called herein a heteropolyligand, shown generically in FIG. 4C.

SEQ ID NOS:37-40 are full length MEK protein substrates or inhibitors. Since MEK undergoes autophosphorylation, MEK is included as a substrate. These sequences have the following public database accession numbers: NP_002746, NP_002737, XP_055766, NP_002736, NP_001744. Each of the sequences represented by these accession numbers is incorporated by reference herein. In SEQ ID NOS:37-40, the positions of the amino acid(s) phosphorylatable by MEK are represented by Xaa. In wild-type proteins, Xaa is serine, threonine, or tyrosine. In the ligands of the invention, Xaa is any amino acid.

SEQ ID NOS:41-48 are partial sequences of SEQ ID NOS:37-39, which represent examples of sequences comprising kinase active site blocker peptide ligand sequences where the location of the MEK phosphorylatable serine, tyrosine, or threonine in the natural polypeptide is designated as Xaa.

SEQ ID NOS:49-51 are partial sequences of SEQ ID NO:38 or SEQ ID NO:40, which represent examples of peptide kinase inhibitors. 5 SEQ ID NOS:41-51 represent examples of monomeric polypeptide ligand sequences.

Amino acid sequences containing Xaa encompass polypeptides where Xaa is any amino acid.

DETAILED DESCRIPTION OF DRAWINGS

FIGS. 3A-3E show examples of heteropolymeric ligands without spacers.

FIGS. 4A-4F show examples of heteropolymeric ligands with spacers.

FIGS. 8A-8G show examples of ligands and polymeric ligands linked to an optional localization signal and an optional epitope tag.

FIGS. 9A-9G show examples of gene constructs where ligands and polyligands are linked to an optional localization signal, an optional epitope tag, and an optional reporter.

FIG. 25 shows the average protein concentration of ligand-beta-galactosidase fusion protein in the lysate of transfected HT-1080 cells.

BRIEF DESCRIPTION OF THE INVENTION

Figure 1A:
FIGS. 1A-1C show examples of homopolymeric ligands without spacers.
Figure 1B:
Figure 1C:
Figure 2A:
FIGS. 2A-2C show examples of homopolymeric ligands with spacers.
Figure 2B:
Figure 2C:
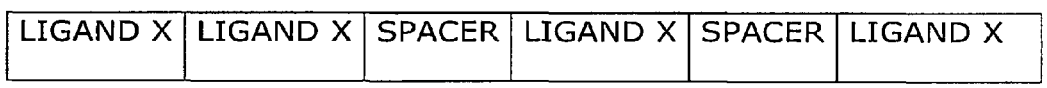
Figure 5A:
FIGS. 5A-5G show examples of ligands and polymeric ligands linked to an optional epitope tag.
Figure 5B:
Figure 5C:
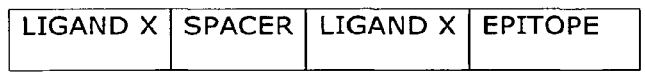
Figure 5D:
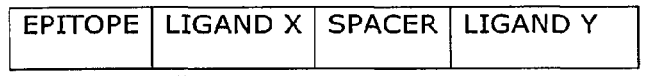
Figure 5E:
Figure 5F:
Figure 5G:
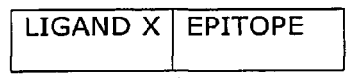
Figure 6A:
FIGS. 6A-6G show examples of ligands and polymeric ligands linked to an optional reporter.
Figure 6B:
Figure 6C:
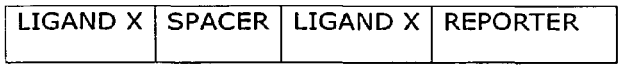
Figure 6D:
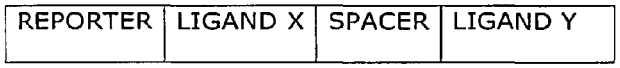
Figure 6E:
Figure 6F:
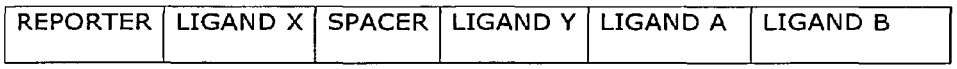
Figure 6G:
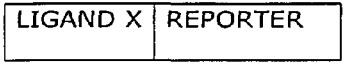
Figure 7A:
FIGS. 7A-7G show examples of ligands and polymeric ligands linked to an optional localization signal.
Figure 7B:
Figure 7C:
Figure 7D:
Figure 7E:
Figure 7F:
Figure 7G:

The invention relates to polypeptide ligands and polyligands for MEK. An aspect of the invention is to provide novel, modular, inhibitors of MEK (hereafter, the term MEK refers to MEK1 and/or MEK2) 30 activity by modifying one or more natural substrates or inhibitors by truncation and/or by amino acid substitution. A further aspect of the invention is the subcellular localization of an MEK inhibitor, ligand, or polyligand by linking to a subcellular localization signal. Various embodiments of the MEK ligands and polyligands are represented in SEQ ID NOS:1-51. More specifically, the invention relates to ligands, homopolyligands, and heteropolyligands that comprise any one or more of SEQ ID NOS:41-51. Additionally, the invention relates to ligands and polyligands comprising one or more partial sequences of SEQ ID NOS:37-40 or any portion thereof. Furthermore, the invention relates to polyligands with at least about 80%, 85%, 90%, 95%, 96%, 97%, 98% and 99% sequence identity to a polyligand comprising one or more of SEQ ID NOS:41-51 or any portion thereof. Furthermore, the invention relates to polyligands with at least about 80%, 85%, 90%, 95%, 96%, 97%, 98% and 99% sequence identity to a polyligand comprising one or more partial sequences of SEQ ID NOS:37-40.

Polyligands, which can be homopolyligands or heteropolyligands, are chimeric ligands composed of two or more monomeric polypeptide ligands. As used herein, the term chimeric refers to an artificial hybrid or fusion polypeptide containing amino acid sequences from two different polypeptides or from different regions of the same polypeptide. An example of a monomeric ligand is the polypeptide represented by SEQ ID NO:43, wherein Xaa is any amino acid. SEQ ID NO:43 is a selected partial sequence of wild-type full length SEQ ID NO:39, wherein the amino acid corresponding to Xaa in the wild-type sequence is a serine, tyrosine, or threonine phosphorylatable by MEK. An example of a homopolyligand is a polypeptide comprising a dimer or multimer of SEQ ID NO:43, wherein Xaa is any amino acid. An example of a heteropolyligand is a polypeptide comprising SEQ ID NO:51 and one or more of SEQ ID NOS:41-50, wherein Xaa is any amino acid. There are numerous ways to combine SEQ ID NOS:41-51 into homopolymeric or heteropolymeric ligands. Furthermore, there are numerous ways to combine additional partial sequences of SEQ ID NOS:37-40 with each other and with SEQ ID NOS:41-51 to make polymeric ligands.

The polyligands of the invention optionally comprise spacer amino acids before, after, or between monomers. SEQ ID NO:1 is an embodiment of a polyligand of the structure A-S1-B-S2-C-S3-D, wherein A is SEQ ID NO:41, B is SEQ ID NO:42, C is SEQ ID NO:49, and D is SEQ ID NO:43, wherein Xaa is alanine or phenylalanine, and wherein S1, S2, and S3 are spacers. This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands.

Monomeric ligands can be categorized into types. One type of monomeric ligand is a polypeptide where at least a portion of the polypeptide is capable of being recognized by MEK as a substrate or pseudosubstrate (active site blocker). The portion of the polypeptide capable of recognition is termed the recognition motif. In the present invention, recognition motifs can be natural or synthetic. Examples of recognition motifs are well known in the art and include, but are not limited to, naturally occurring MEK substrates and pseudosubstrate motifs (SEQ ID NOS:41-48 and partial sequences of SEQ ID NOS:37-39 containing a recognition motif). Another type of monomeric ligand is a polypeptide where at least a portion of the polypeptide is capable of associating with and inhibiting MEK at a location other than the MEK active site.

A polymeric ligand comprises two or more monomeric ligands linked together to create a chimera.

A homopolymeric ligand is a polymeric ligand where each of the monomeric ligands is identical in amino acid sequence, except that a phosphorylatable residue may be substituted or modified in one or more of the monomeric ligands.

A heteropolymeric ligand is a polymeric ligand where some of the monomeric ligands do not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclese activity. The flanking sequences optionally provide unique cloning sites within a vector and optionally provide directionality of subsequence cloning. Further, the nucleic acids of the invention are optionally incorporated into vector polynucleotides. The ligands, polyligands, and polynucleotides of this invention have utility as research tools and/or therapeutics.

DETAILED DESCRIPTION OF THE INVENTION

The present invention relates to ligands and polyligands that are MEK modulators. An aspect of the invention is to provide novel, monomeric and chimeric, modular inhibitors of MEK activity by modifying one or more natural substrates or inhibitors by truncation and/or by amino acid substitution. A further aspect of the invention is the subcellular localization of an MEK inhibitor, ligand, or polyligand by linking to a subcellular localization signal. Various embodiments of ligands and polyligands are represented in SEQ ID NOS:1-51. Polyligands are chimeric ligands comprising two or more monomeric polypeptide ligands. An example of a monomeric ligand is the polypeptide represented by SEQ ID NO:42, wherein Xaa is any amino acid. SEQ ID NO:42 is a selected partial sequence of parental full length SEQ ID NO:37, wherein the amino acid corresponding to Xaa in the parent sequence is a serine, tyrosine, or threonine phosphorylatable by MEK. Another example of a monomeric ligand is the polypeptide represented by SEQ ID NO:49. Another example of a monomeric ligand is the polypeptide represented by SEQ ID NO:46. Each of SEQ ID NOS:41-51 represents an individual polypeptide ligand in monomeric form, wherein Xaa is any amino acid. SEQ ID NOS:41-54 are selected examples of partial sequences of SEQ ID NOS:37-40, however, other partial sequences of SEQ ID NOS:37-40 containing a recognition motif or binding association motif may also be utilized as monomeric ligands. Monomeric ligand partial sequences of SEQ ID NOS:37-40 may be wild-type partial sequences. Additionally, monomeric ligand partial sequences of SEQ ID NOS:37-40 may have MEK phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:41-51. Furthermore, monomeric ligands and polyligands may have at least about 80%, 85%, 90%, 95%, 96%, 97%, 98% and 99% sequence identity to a partial sequence of SEQ ID NOS:37-40.

An example of a homopolyligand is a polypeptide comprising a dimer or multimer of SEQ ID NO:50. Another example of a homopolyligand is a polypeptide comprising a dimer or multimer of SEQ ID NO:51. An example of a heteropolyligand is a polypeptide comprising SEQ ID NO:41 and one or more of SEQ ID NOS:42-51, wherein Xaa is any amino acid. There are numerous ways to combine SEQ ID NOS:41-51 into homopolymeric or heteropolymeric ligands. Furthermore, there are numerous ways to combine additional partial sequences of SEQ ID NOS:37-40 with each other and with SEQ ID NOS:41-51 to make polymeric ligands. Polyligands may comprise any two or more of SEQ ID NOS:41-51, wherein Xaa is any amino acid. SEQ ID NOS:41-51 are selected examples of partial sequences of SEQ ID NOS:37-40, however, additional partial sequences, wild-type or mutated, may be utilized to form polyligands. The instant invention is directed to all possible combinations of homopolyligands and heteropolyligands without limitation.

SEQ ID NOS:41-48 show proteins that contain at least one serine or threonine residue phosphorylatable by MEK, the positions of which are represented by Xaa. Since MEK autophosphorylates, MEK itself is included as a substrate. SEQ ID NOS:41-48 are partial sequences of SEQ ID NOS:37-39 where, again, the locations of the MEK phosphorylatable residues are represented by Xaa. In nature, Xaa is, generally speaking, serine, tyrosine, or threonine. In one embodiment of the instant invention, Xaa can be any amino acid. Ligands where Xaa is serine, tyrosine, or threonine can be used as part of a polyligand; however, in one embodiment, at least one phosphorylatable serine, tyrosine, or threonine is replaced with another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, or tryptophan. The Xaa may also be a non-naturally occurring amino acid. In another embodiment, the MEK phosphorylatable residue(s) are replaced by alanine. In another embodiment, the MEK phosphorylatable residue(s) are replaced by phenylalanine. The ligands and polyligands of the invention are designed to modulate the endogenous effects of MEK.

In general, ligand monomers based on natural MEK substrates are built by identifying a putative MEK phosphorylation recognition motif in a MEK substrate. Sometimes it is desirable to modify the phosphorylatable residue to an amino acid other than serine, tyrosine, or threonine. Additional monomers include the MEK recognition motif as well as amino acids adjacent and contiguous on either side of the MEK recognition motif. Monomeric ligands may therefore be any length provided the monomer includes the MEK recognition motif. For example, the monomer may comprise an MEK recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the recognition motif.

For example, in one embodiment, the invention comprises a polypeptide inhibitor of MEK comprising at least one copy of a peptide selected from the group consisting of:

a) a peptide at least 80% identical to a peptide comprising amino acid residues corresponding to amino acid residues 165-203 of SEQ ID NO:39, wherein the amino acid residue corresponding to amino acid residue 185 and/or 187 of SEQ ID NO:39 is an amino acid residue other than serine, tyrosine, or threonine;

b) a peptide at least 80% identical to a peptide comprising amino acid residues corresponding to amino acid residues 169-200 of SEQ ID NO:39, wherein the amino acid residue corresponding to amino acid residue 185 and/or 187 of SEQ ID NO:39 is an amino acid residue other than serine, tyrosine, or threonine;

c) a peptide at least 80% identical to a peptide comprising amino acid residues corresponding to amino acid residues 174-196 of SEQ ID NO:39, wherein the amino acid residue corresponding to amino acid residue 185 and/or 187 of SEQ ID NO:39 is an amino acid residue other than serine, tyrosine, or threonine; and d) a peptide at least 80% identical to a peptide comprising amino acid residues corresponding to amino acid residues 179-194 of SEQ ID NO:39, wherein the amino acid residue corresponding to amino acid residue 185 and/or 187 of SEQ ID NO:39 is an amino acid residue other than serine, tyrosine, or threonine.

As used herein, the terms "correspond(s) to" and "corresponding to," as they relate to sequence alignment, are intended to mean enumerated positions within a reference protein, e.g., ERK1 (SEQ ID NO:38), and those positions that align with the positions on the reference protein. Thus, when the 25 amino acid sequence of a subject peptide is aligned with the amino acid sequence of a reference peptide, e.g., SEQ ID NO:38, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate for MEK, such as substrates identified by SEQ ID NOS:37-39. Furthermore, if the substrate has more than one recognition motif, then more than one monomer may be identified therein.

Another embodiment of the invention is a nucleic acid molecule comprising a polynucleotide sequence encoding at least one copy of a ligand peptide.

Another embodiment of the invention is an isolated polypeptide homopolyligand, wherein the homopolyligand modulates MEK activity.

Another embodiment of the invention is an isolated polypeptide heteropolyligand, wherein the heteropolyligand modulates MEK activity.

Another embodiment of the invention is a nucleic acid molecule wherein the polynucleotide sequence 15 encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a 25 nucleic acid molecule encoding at least one copy of a ligand or polyligand.

Another embodiment of the invention is a method of inhibiting MEK in a cell comprising transfecting a vector comprising a nucleic acid molecule encoding at least one copy of a ligand or polyligand into a host cell and culturing the transfected host cell under conditions suitable to produce at least one copy of the ligand or polyligand.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring MEK recognition motif that has been modified by addition, deletion, or substitution of one or more amino acids in the primary structure (amino acid sequence) of the motif. For example, a modified MEK recognition motif may be a motif where the phosphorylatable amino acid has been modified to a non-phosphorylatable amino acid. The terms "protein," "peptide" and "polypeptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of amino acids of the query sequence that are N- and C-terminus to the reference sequence that are not matched/aligned, as a percent of the total amino acids of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query.

In this case the percent identity calculated by FASTDB is not manually corrected.

The polyligands of the invention optionally comprise spacer amino acids before, after, or between monomers. The length and composition of the spacer may vary. An example of a spacer is glycine, alanine, polyglycine, or polyalanine. Specific examples of spacers used between monomers in SEQ ID NO:1 are the five amino acid spacers PGAAG (SEQ ID NO: 52) and PAGGA (SEQ ID NO: 54). In the instance of SEQ ID NO:1, the proline-containing spacers are intended to break secondary structure. Spacer amino acids may be any amino acid and are not limited to these alanine, glycine, and proline-containing examples. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell (See FIGS. 5A-5G, FIGS. 6A-6G, FIGS. 7A-7G, and FIGS. 8A-8G).

Non-limiting examples of epitope tags are FLAG™, HA (hemagluttinin), c-Myc and His6. Non-limiting examples of reporters are alkaline phosphatase, galactosidase, peroxidase, luciferase and fluorescent proteins. Non-limiting examples of cellular localizations are sarcoplamic reticulum, endoplasmic reticulum, mitochondria, golgi apparatus, nucleus, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Peptides can also be synthesized utilizing non-automated peptide synthesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized.

Additionally, non-standard amino acids and amino acids modified with lipids, carbohydrates, phosphate or other molecules may be used as precursors to peptide synthesis.

The ligands of the invention have therapeutic utility with or without localization signals. However, ligands linked to localization signals have utility as subcellular tools or therapeutics. For example, 25 ligands depicted generically in FIGS. 7A-7G represent ligands with utility as subcellular tools or therapeutics. MEK ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 10A:
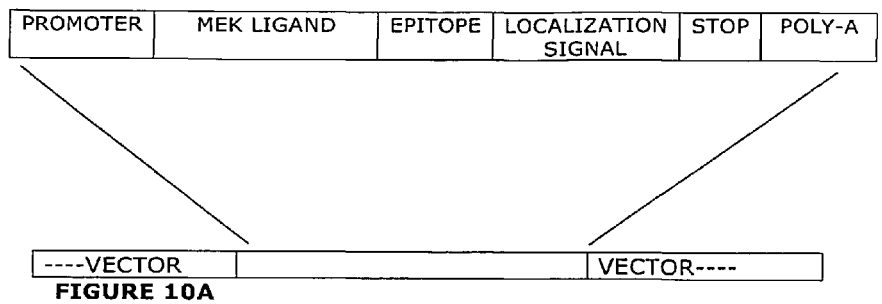
FIGS. 10A-10D show examples of vectors containing ligand gene constructs.
Figure 10B:
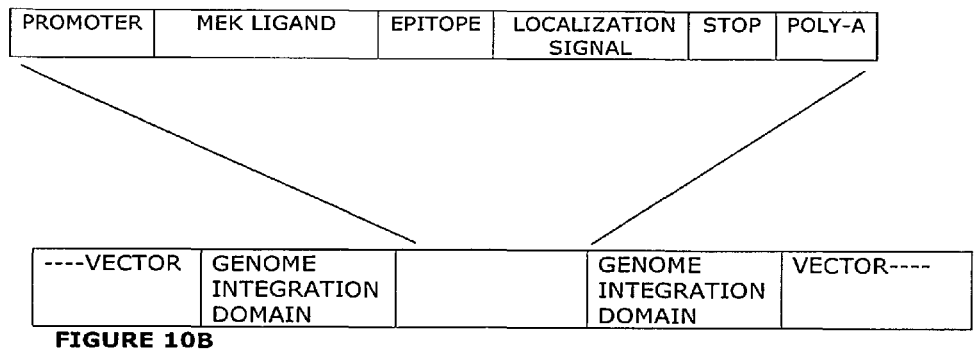
Figure 10C:
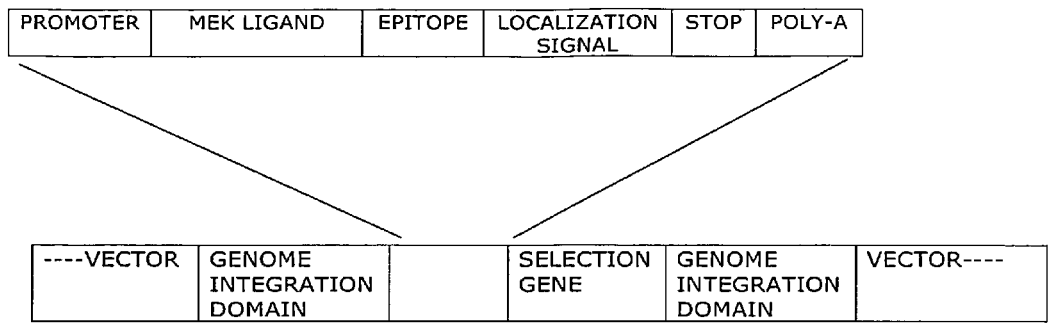

FIG. 10A shows a vector containing an MEK ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the transgene, wherein the promoter and codons of the transgene are optimized for the host organism. The vector containing a ligand gene construct of FIG. 10A is also useful for recombinant expression of polypeptides in fermentable organisms adaptable for small or large scale production, wherein the promoter and codons of the transgene are optimized for the fermentation host organism.

Figure 10D:
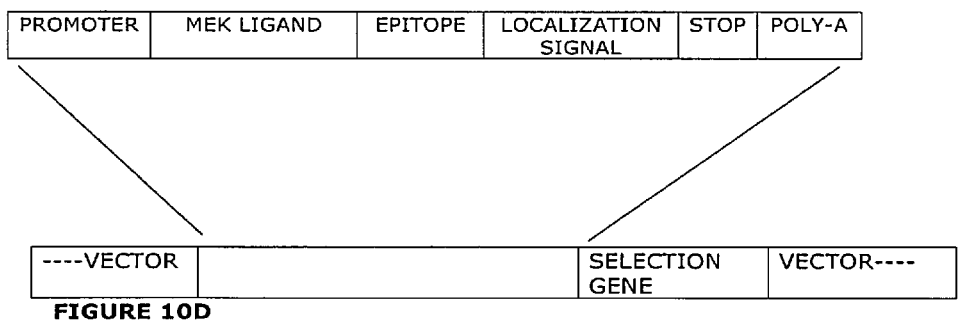

FIG. 10D shows a vector containing an MEK ligand gene construct useful for generating stable cell lines.

The invention also encompasses polynucleotides comprising nucleotide sequences encoding ligands, homopolyligands, and heteropolyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclese activity. The flanking sequences optionally provide cloning sites within a vector. The restriction sites can include, but are not limited to, any of the commonly used sites in most commercially available cloning vectors. Examples of such sites are those recognized by BamHI, ClaI, EcoRI, EcoRV, SpeI, AflII, NdeI, NheI, XbaI, XhoI, SphI, NaeI, SexAI, HindIII, HpaI, and PstT restriction endonucleases. Sites for cleavage by other restriction enzymes, including homing endonucleases, are also used for this purpose. The polynucleotide flanking sequences also optionally provide directionality of partial sequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealed. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promotor, a non-constitutive promotor, a tissue-specific promotor (constitutive or non-constitutive) or a selectively controlled promotor. Different selectively controlled promotors are controlled by different mechanisms. For example, RheoSwitch® is an inducible promotor system available from New England Biolabs.

Temperature sensitive promotors can also be used to increase or decrease gene expression. An embodiment of the invention comprises a ligand or polyligand gene construct whose expression is controlled by an inducible promotor. In one embodiment, the inducible promotor is tetracycline controllable.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular partial sequence cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

Figure 11:
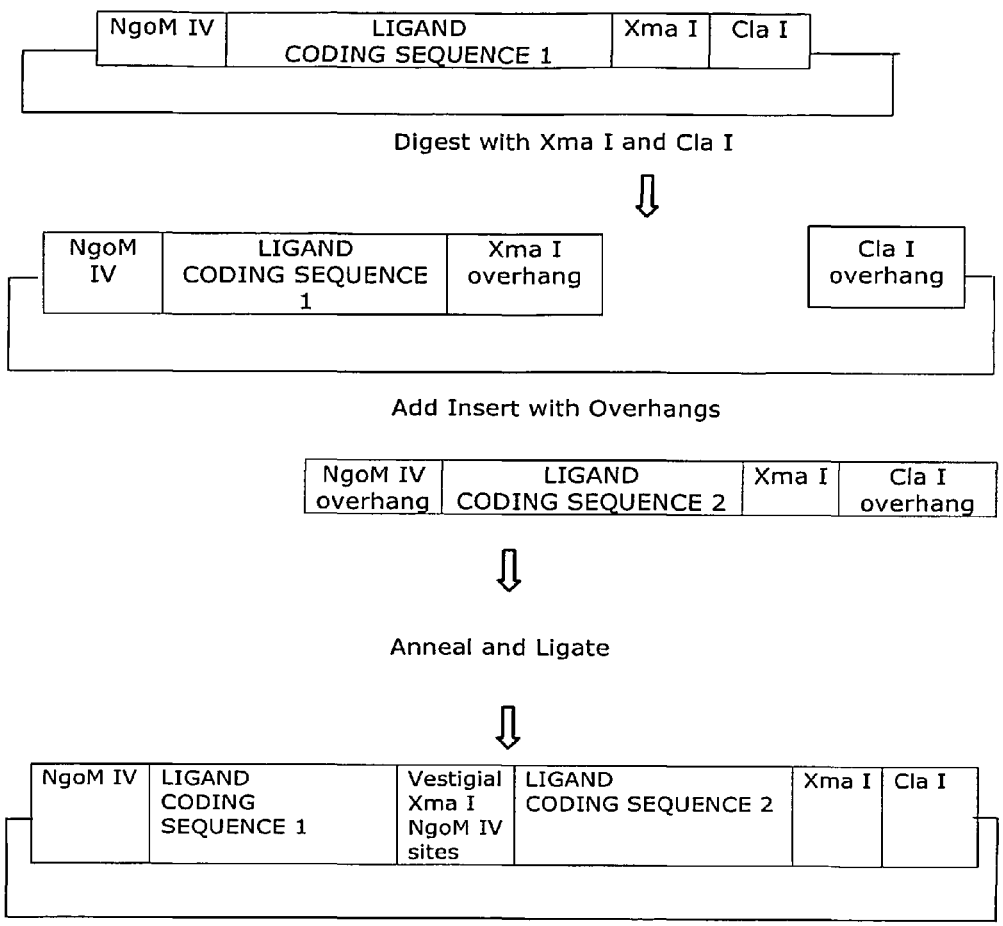
FIG. 11 shows an example of a sequential cloning process useful for combinatorial synthesis of polyligands.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to form a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 11.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endouclease site that does not generate sticky ends compatible with either of the first two. When such criteria are utilized as a system for sequential, directional cloning, ligands, polyligands and other coding regions or expression components can be combinatorially assembled as desired. The same sequential process can be utilzed 5 for epitope, reporter, and/or localization signals.

Polyligands and methods of making polyligands that modulate MEK activity are disclosed. Therapeutics include delivery of purified ligand or polyligand with or without a localization signal to a cell. Alternatively, ligands and polyligands with or without a localization signals are delivered via adenovirus, lentivirus, adeno-associated virus, or other viral constructs that express protein product in a cell.

EXAMPLE 1

A polypeptide comprising a heteropolyligand, an endoplasmic reticulum cellular localization signal, and a His6 epitope is synthesized. Examples of such polypeptides are generically represented by FIGS. 8A, 8B, 8D, 8E and 8F. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

EXAMPLE 2

A transgene is constructed using a cytomegalovirus (CMV) promoter to direct expression of a fusion protein comprising SEQ ID NO:49, SEQ ID NO:48, SEQ ID NO:41, wherein Xaa is alanine (POLYLIGAND), green fluorescent protein (REPORTER), and a plasma membrane localization signal (LOCALIZATION SIGNAL). Such a transgene is generically represented by FIG. 9C. The transgene is transfected into cells for transient expression. Verification of expression and location is performed by visualization of green fluorescent protein by confocal microscopy.

EXAMPLE 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode an MEK ligand, a FLAG™ epitope, and a nuclear localization signal. The MEK ligand is a monomeric ligand, homopolymeric ligand or heteropolymeric ligand as described herein. Nucleotide sequences encoding a FLAG™ epitope are placed downstream of nucleotide sequences encoding the MEK ligand. Finally, nucleotide sequences encoding the localization signal are placed downstream of those encoding the FLAG™ epitope. The assembled gene expression unit is subsequently subcloned into an expression vector, such as that shown in FIG. 10A, and used to transiently transfect cells. Verification is performed by immunohistochemical staining using an anti-FLAG™ antibody.

EXAMPLE 4

Modulation of MEK cellular function by subcellularly localized MEK polyligand is illustrated. A transgene construct containing nucleic acids that encode a polyligand fusion protein, epitope, and endoplasmic reticulum localization signal is made. The expression unit contains nucleotides that encode SEQ ID NO:25 (POLYLIGAND), a c-Myc epitope (EPITOPE), and a nuclear localization signal (LOCALIZATION SIGNAL). This expression unit is subsequently subcloned into a vector between a EF1alpha promoter and an SV40 polyadenylation signal. The completed transgenecontaining expression vector is then used to transfect cells. Inhibition of MEK activity is demonstrated by measuring phosphorylation of endogenous substrates against controls and/or observing phenotypes.

EXAMPLE 5

Ligand function and localization is demonstrated in vivo by making a transgene construct used to generate mice expressing a ligand fusion protein targeted to the nucleus. The transgene construct is shown generically in FIG. 10B. The expression unit contains nucleotides that encode a tetramer of SEQ ID NO:33, a hemagluttinin epitope, and a nuclear localization signal. This expression unit is subsequently subcloned into a vector between nucleotide sequences including an inducible promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 5 harbor the transgene in their genomes.

Test 2: Tissue homogenates are prepared for Western blot analysis. This experiment demonstrates the transgene is expressed in tissues of transgenic mice because hemagluttinin epitope is detected in transgenic homogenates but not in non-transgenic homogenates.

Test 3: Function is assessed by phenotypic observation or analysis against controls after induction of expression.

These examples demonstrate delivery of ligands to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

EXAMPLE 6

Fusion proteins were constructed with ligands of the present invention fused to beta-galactosidase.

Figure 12:
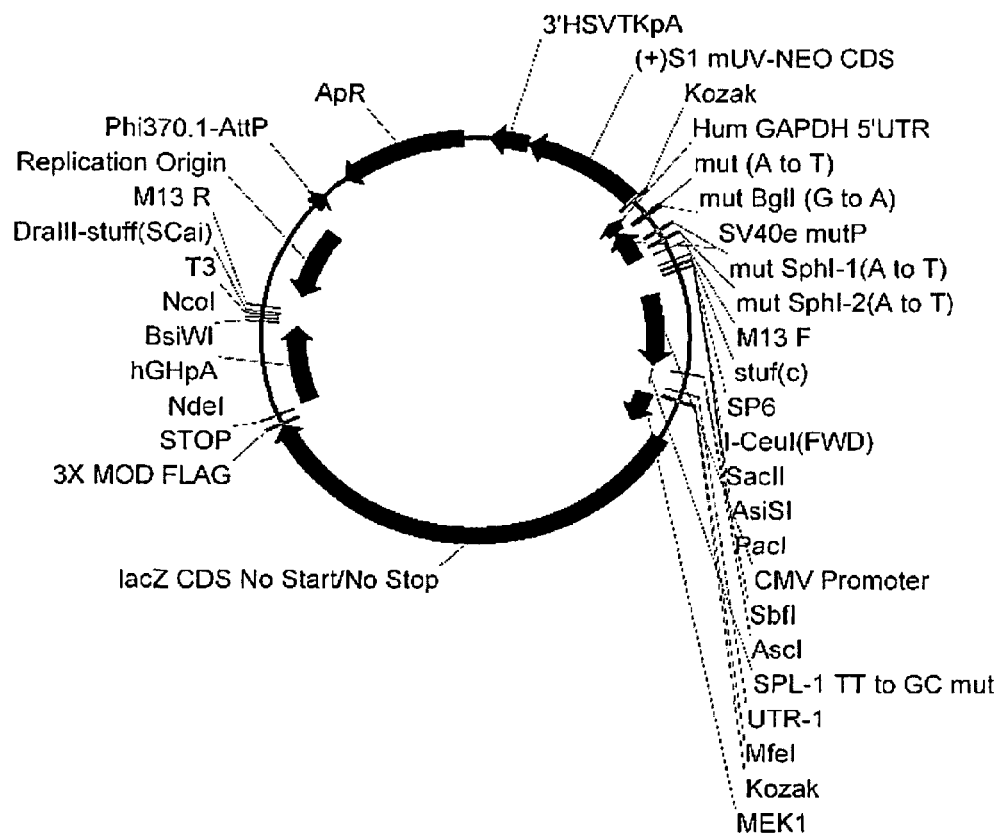
FIGS. 12-24 show diagrams of vectors containing gene constructs for ligand-beta-galactosidase fusion proteins of the invention.

FIG. 12 represents a vector that comprises a polynucleotide that encodes the polyligand of SEQ ID NO:33. In the vector of FIG. 12, the polynucleotide encoding the ligand of SEQ ID NO:33 is linked to a polynucleotide encoding beta-galactosidase to create a ligand fusion protein coding sequence.

Figure 13:
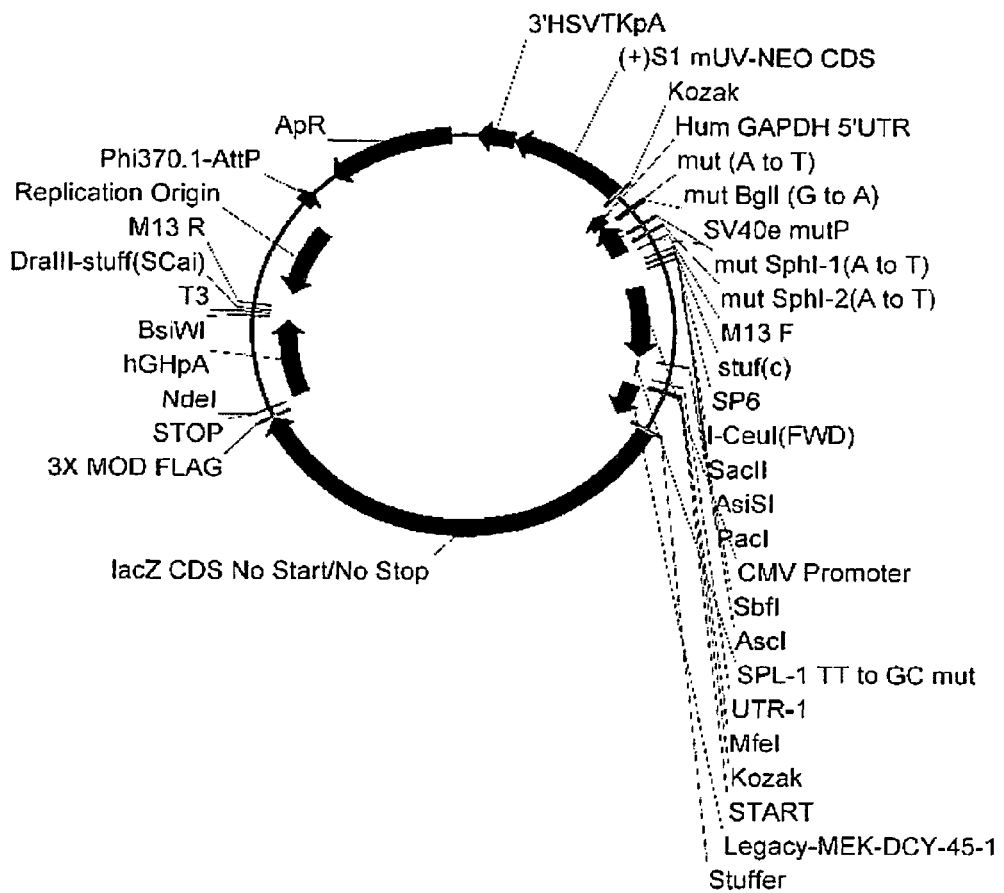

FIG. 13 represents a vector that comprises the polynucleotide of SEQ ID NO:2, which encodes the ligand of SEQ ID NO:1. In the vector of FIG. 13, the polynucleotide of SEQ ID NO:2 is linked to a polynucleotide encoding beta-galactosidase to create a ligand fusion protein coding sequence.

Figure 14:
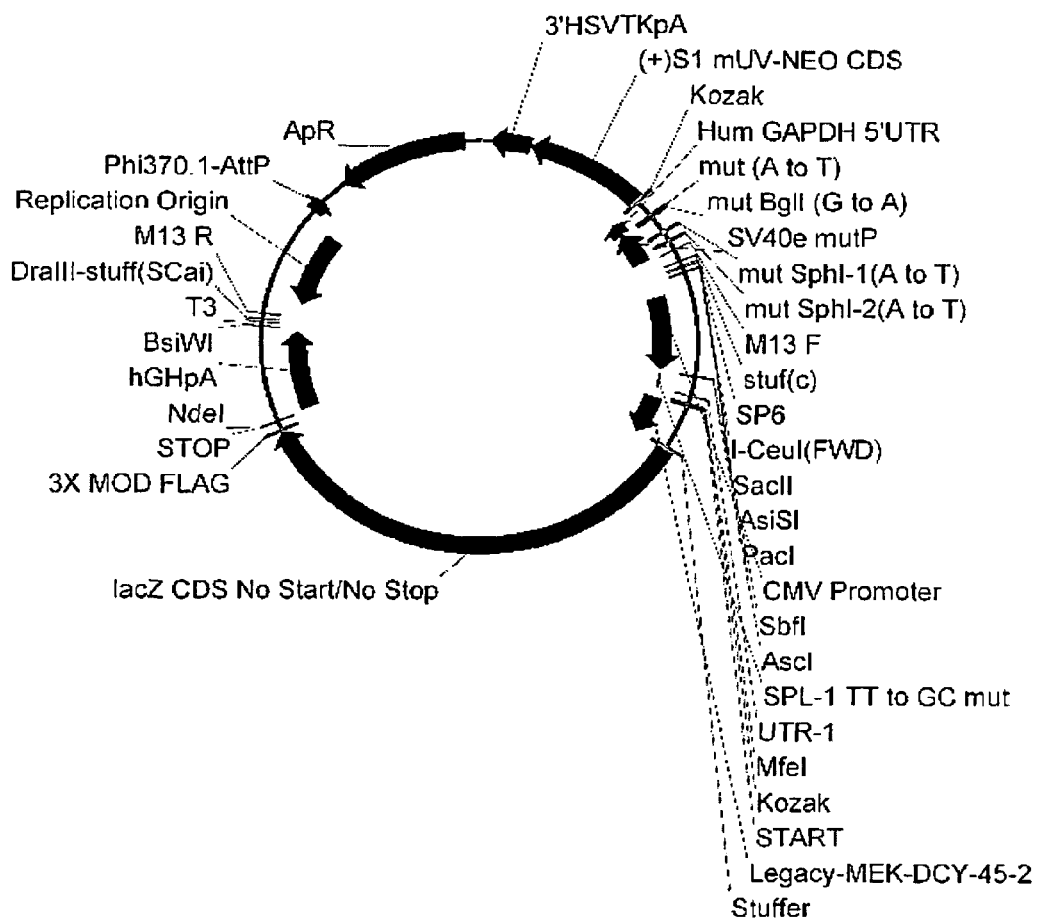

FIG. 14 represents a vector that comprises the polynucleotide of SEQ ID NO:6, which encodes the ligand of SEQ ID NO:5. In the vector of FIG. 14, the polynucleotide of SEQ ID NO:6 is linked to a polynucleotide encoding beta-galactosidase to create a ligand fusion protein coding sequence.

Figure 15:
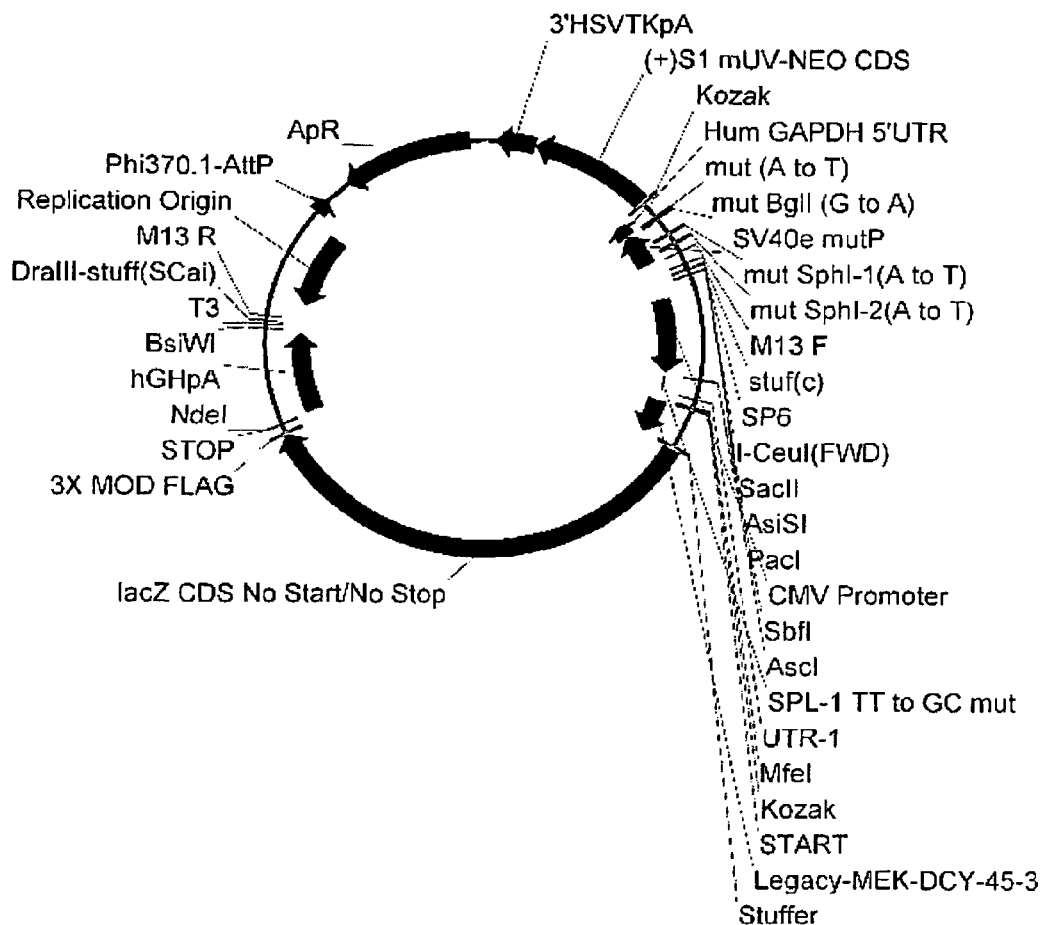

FIG. 15 represents a vector that comprises the polynucleotide of SEQ ID NO:10, which encodes the ligand of SEQ ID NO:9. In the vector of FIG. 15, the polynucleotide of SEQ ID NO:10 is linked to a polynucleotide encoding beta-galactosidase to create a ligand fusion protein coding sequence.

Figure 16:
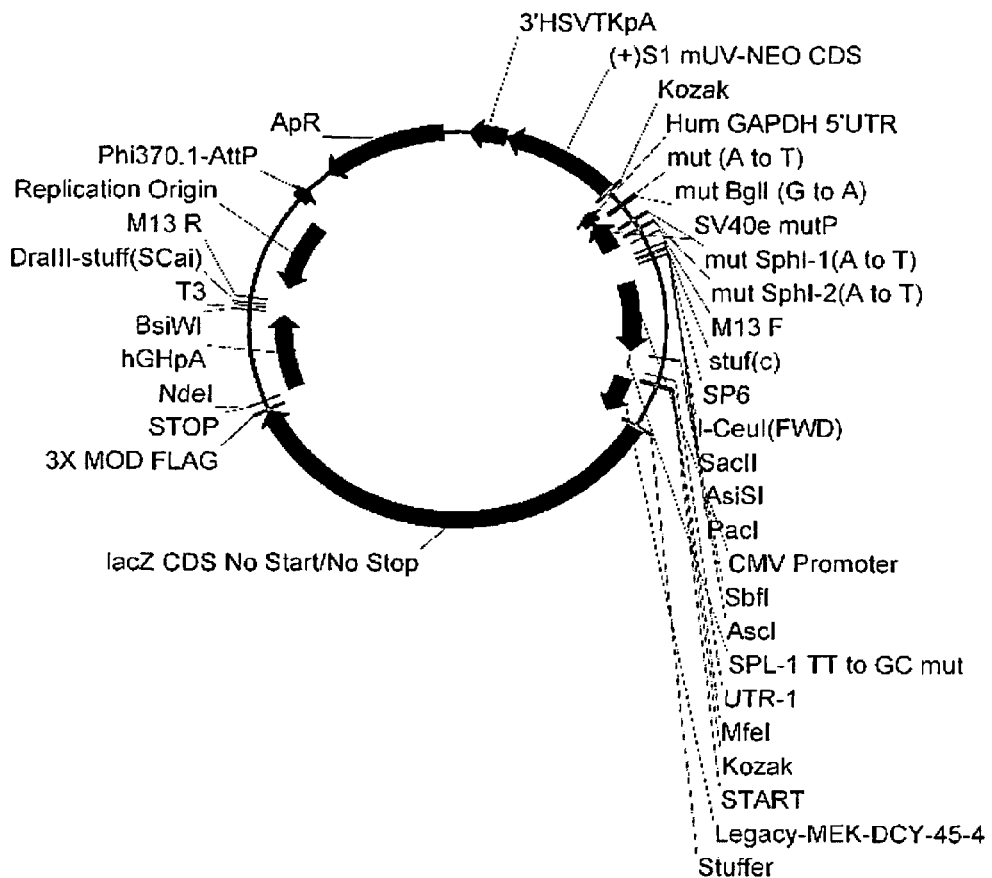

FIG. 16 represents a vector that comprises the polynucleotide of SEQ ID NO:14, which encodes the ligand of SEQ ID NO:13. In the vector of FIG. 16, the polynucleotide of SEQ ID NO:14 is linked to a polynucleotide encoding beta-galactosidase to create a ligand fusion protein coding sequence.

Figure 17:
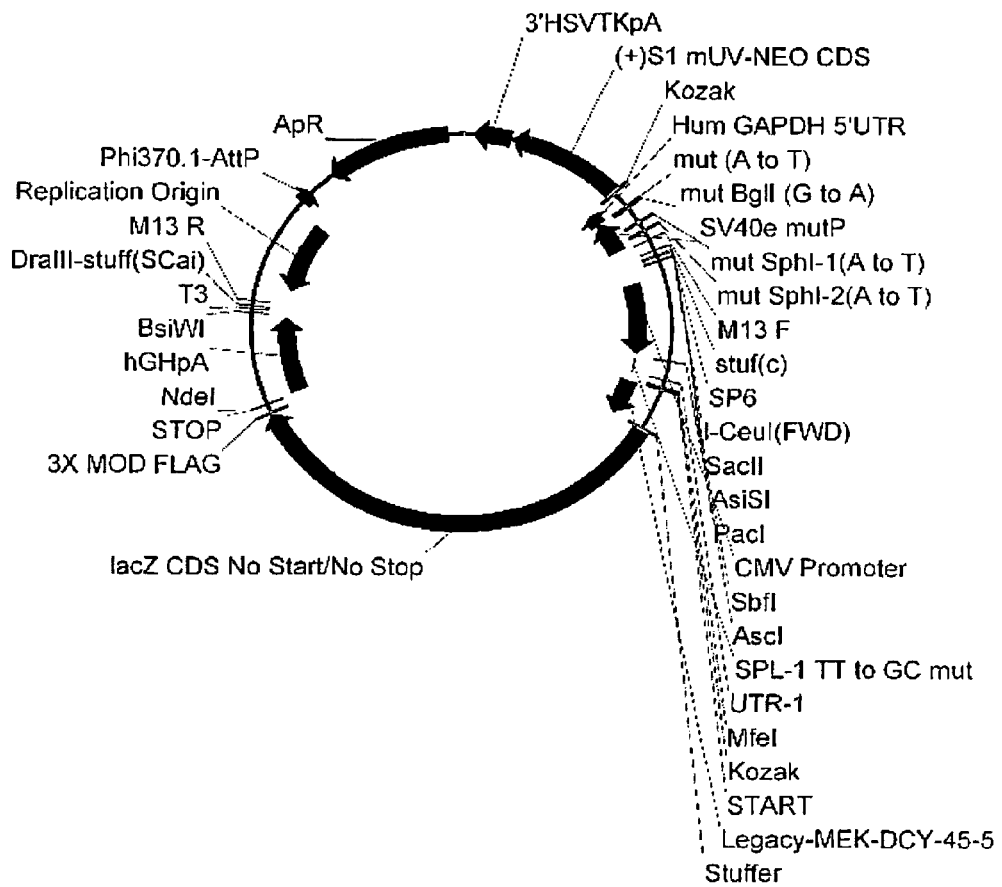

FIG. 17 represents a vector that comprises the polynucleotide of SEQ ID NO:18, which encodes the ligand of SEQ ID NO:17. In the vector of FIG. 17, the polynucleotide of SEQ ID NO:18 is linked to a polynucleotide encoding beta-galactosidase to create a ligand fusion protein coding sequence.

Figure 18:
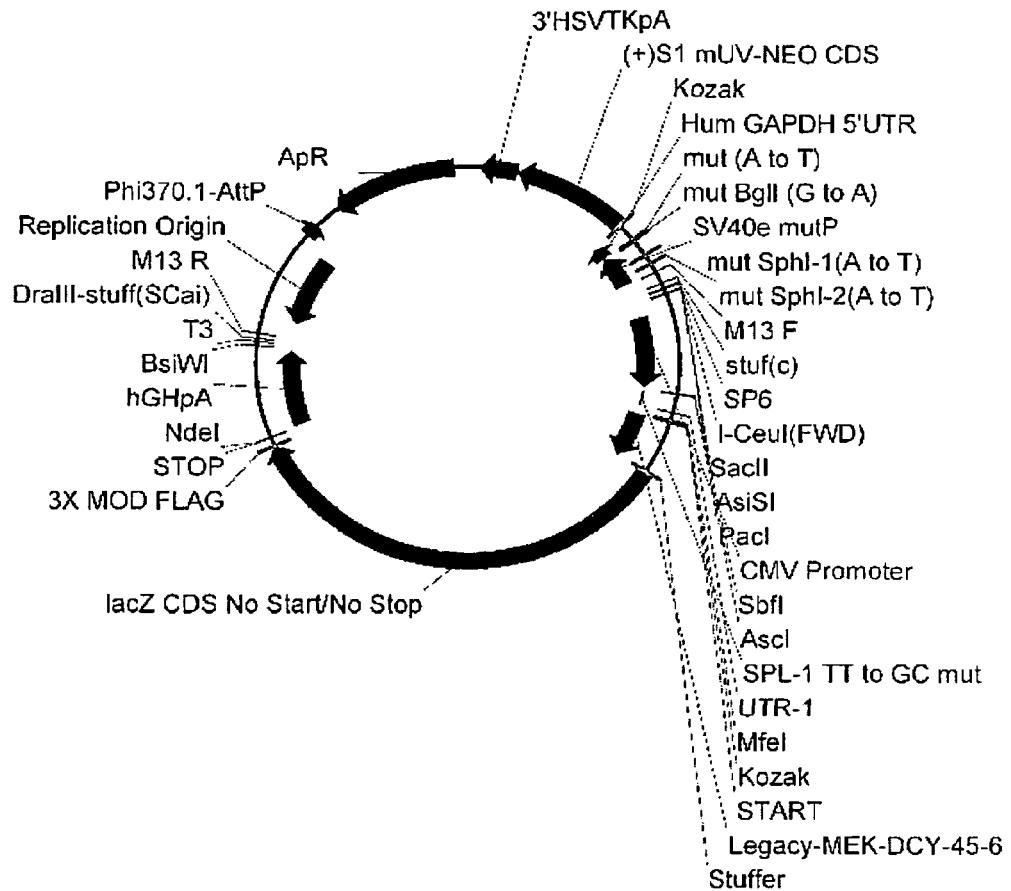

FIG. 18 represents a vector that comprises the polynucleotide of SEQ ID NO:22, which encodes the ligand of SEQ ID NO:21. In the vector of FIG. 18, the polynucleotide of SEQ ID NO:22 is linked to a polynucleotide encoding beta-galactosidase to create a ligand fusion protein coding sequence.

Figure 19:
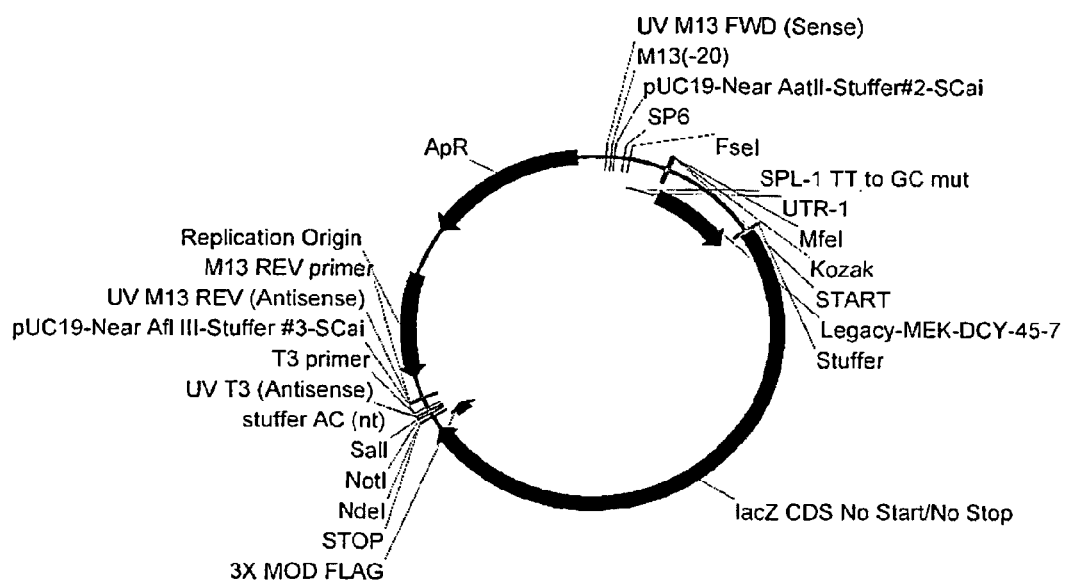

FIG. 19 represents a vector that comprises SEQ ID NO:26, which encodes the ligand of SEQ ID NO:25. In the vector of FIG. 19, the polynucleotide of SEQ ID NO:26 is linked to a polynucleotide encoding beta-galactosidase to create a ligand fusion protein coding sequence.

Figure 20:
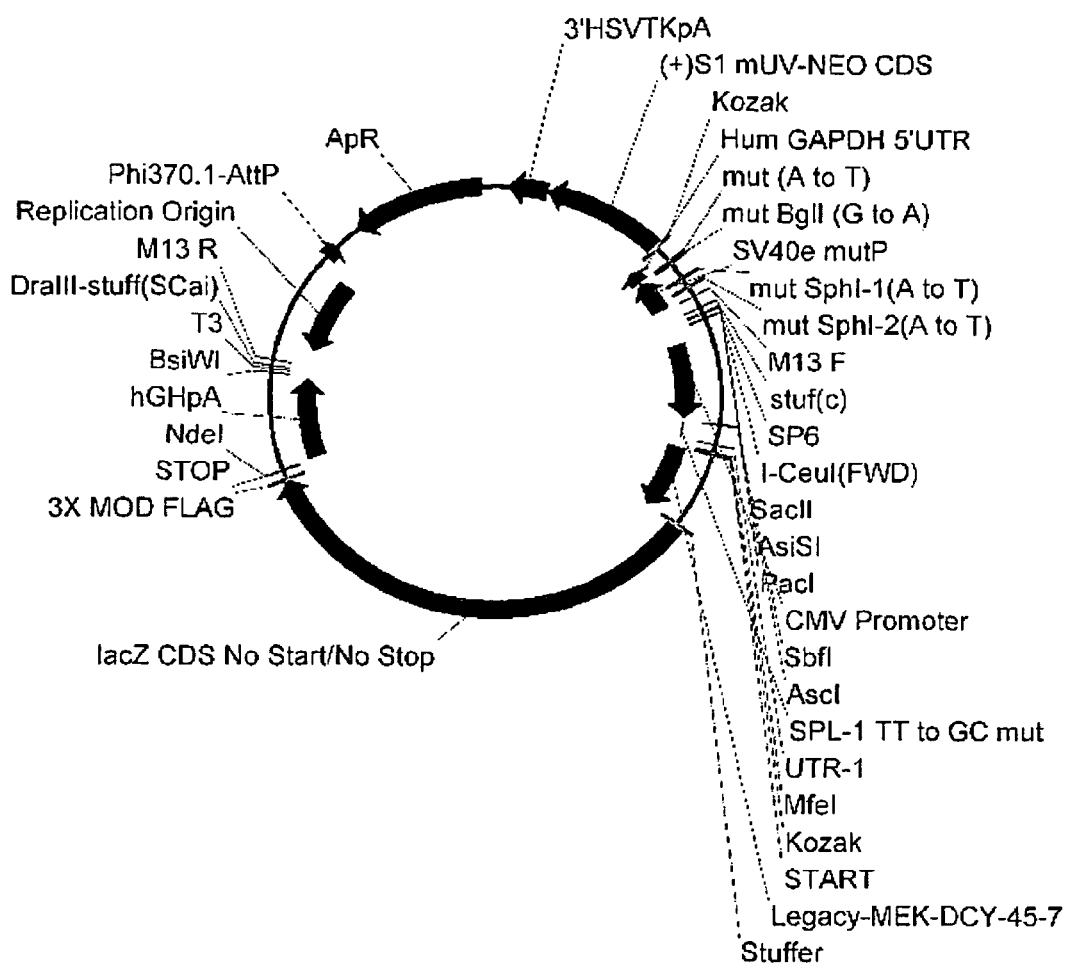

FIG. 20 represents another vector that comprises SEQ ID NO:26, which encodes the ligand of SEQ ID NO:25. In the vector of FIG. 20, the polynucleotide of SEQ ID NO:26 is linked to a polynucleotide encoding beta-galactosidase to create a ligand fusion protein coding sequence.

Figure 21:
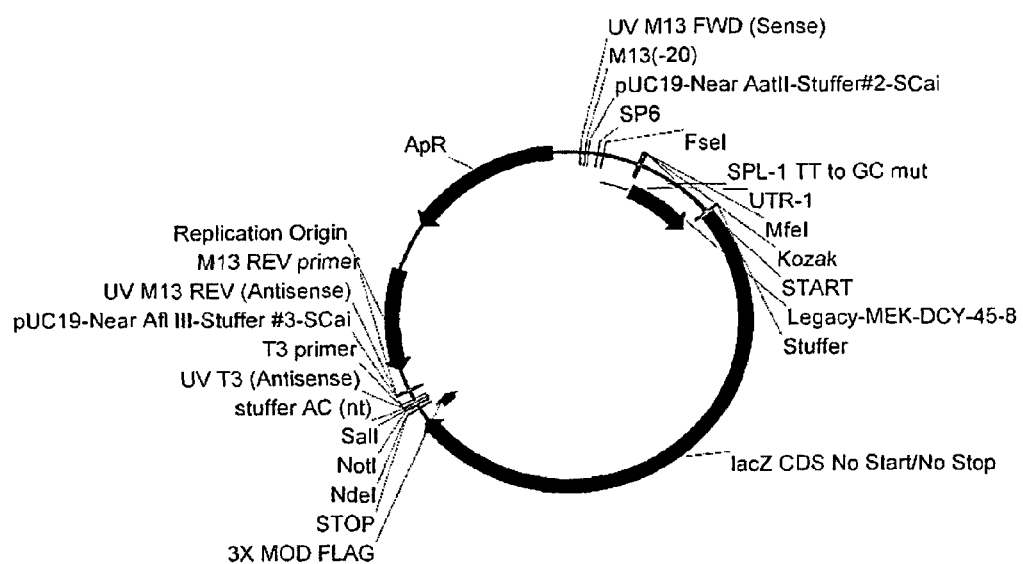

FIG. 21 represents a vector that comprises SEQ ID NO:30, which encodes the ligand of SEQ ID NO:29. In the vector of FIG. 21, the polynucleotide of SEQ ID NO:30 is linked to a polynucleotide encoding beta-galactosidase to create a ligand fusion protein coding sequence.

Figure 22:
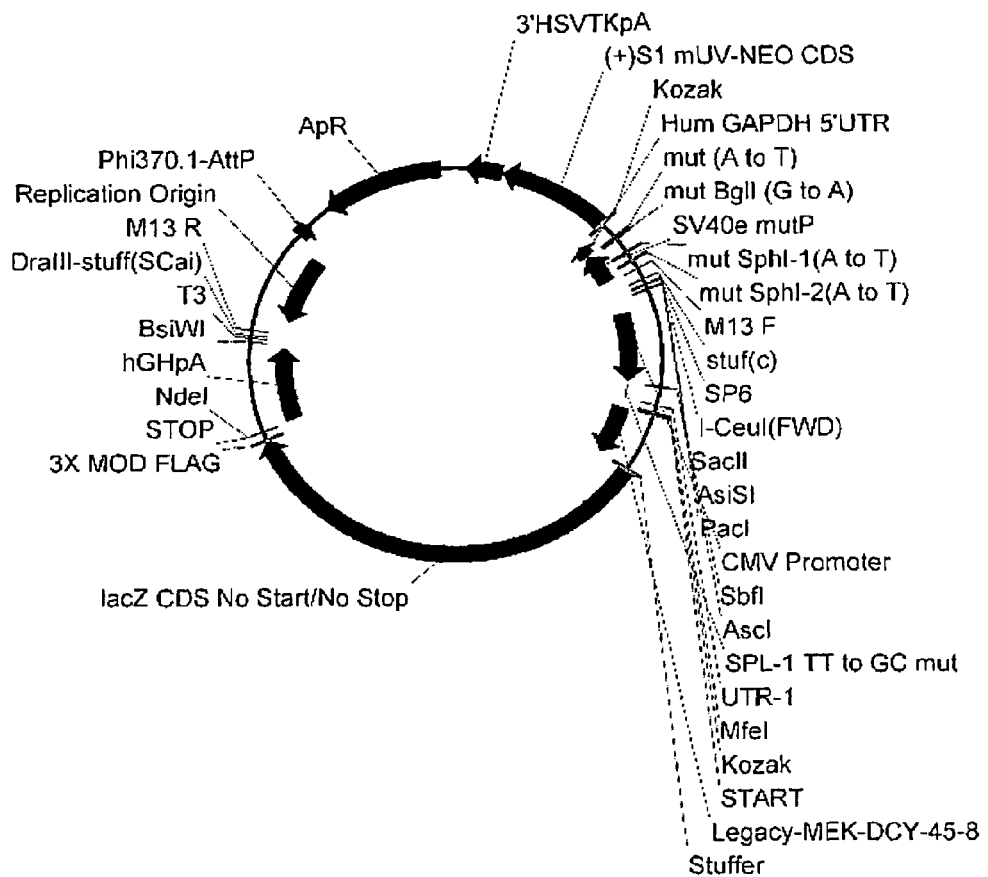

FIG. 22 represents another vector that comprises SEQ ID NO:30, which encodes the ligand of SEQ ID NO:29. In the vector of FIG. 22, the polynucleotide of SEQ ID NO:30 is linked to a polynucleotide encoding beta-galactosidase to create a fusion protein coding sequence.

Figure 23:
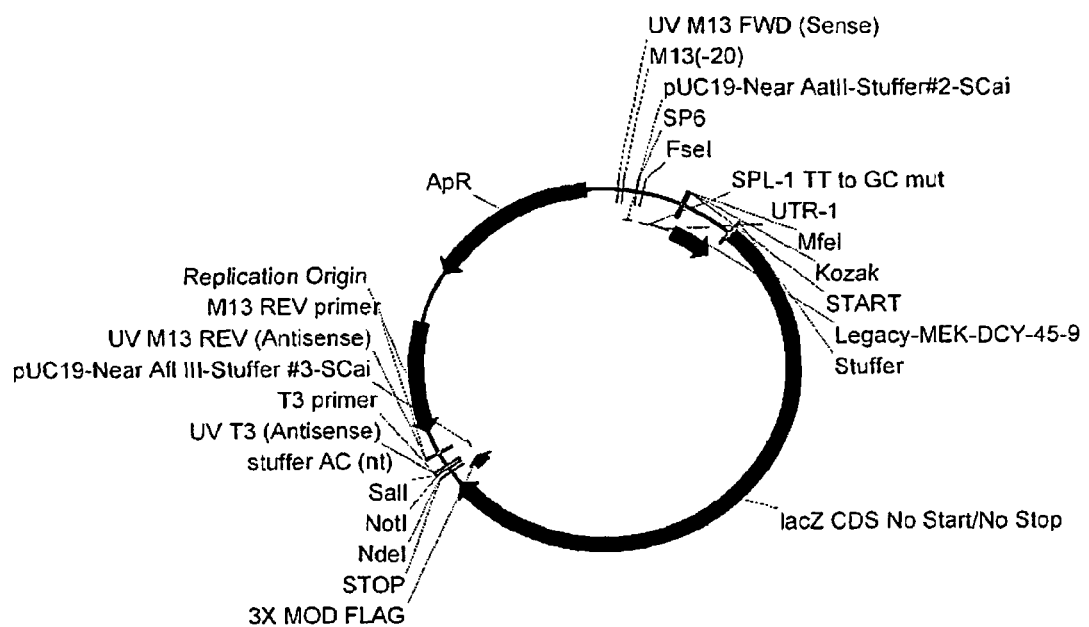

FIG. 23 represents a vector that comprises SEQ ID NO:34, which encodes the ligand of SEQ ID NO:33. In the vector of FIG. 23, the polynucleotide of SEQ ID NO:34 is linked to a polynucleotide encoding beta-galactosidase to create a ligand fusion protein coding sequence.

Figure 24:
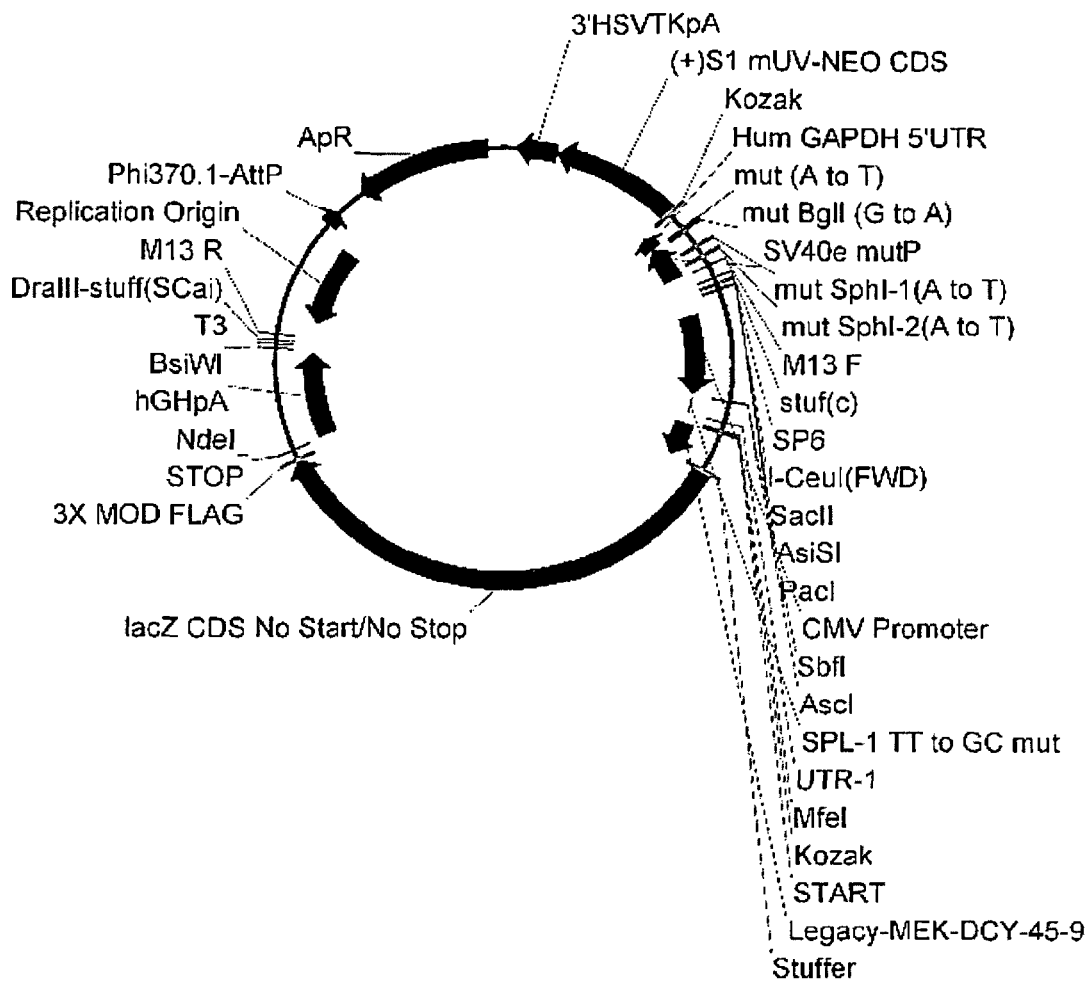

FIG. 24 represents another vector that comprises SEQ ID NO:34, which encodes the ligand of SEQ ID NO:33. In the vector of FIG. 24, the polynucleotide of SEQ ID NO:34 is linked to a polynucleotide encoding beta-galactosidase to create a ligand fusion protein coding sequence.

The vectors of FIGS. 12-24 were transfected into the mammalian cell line HT1080. A vector comprising a polynucleotide encoding the MEK substrate ERK was also transfected in HT1080 cells. Transfections were performed using Fugene6 reagent—purchased from Roche (Basel, Switzerland)—according to the manufacture specifications. Briefly, the cells were seeded into 6-well plates at a density of 300,000 per well in 2 ml of DMEM with 10% of FBS. 24 hours later, the transfection complexes per each well were prepared by mixing of 1 ug of plasmid DNA with 3 ul of Fugene6 which resulted in 100 ul of the DNA/lipid complex dissolved in the serum free DMEM. After 30 minutes of incubation allowing to properly form the complex 100 ul of the mixture was added to each well of cells growing in 2 ml of medium. Cells were exposed to the DNA/lipid complexes for 24 hours and subsequently lyzed for the RNA and protein analysis.

FIG. 25 shows the results of protein analyses of the lysate for ligand fusion proteins encoded by the vectors of FIGS. 12-18 and FIGS. 20, 22 and 24. The ligand fusion proteins were quantified using the beta-galactosidase ELISA kit from Roche (#11539426001) according to kit protocol. Values represent the average of two replicates, except for VVN-40647 which represents the value of 1 replicate.

The lysates containing ligand fusion proteins were assayed in a protein dot-blot binding assay for the detection of binding to MEK1 protein or MEK2 protein using the following protocol:

1. Soak a nitrocellulose membrane in TBS for 5 minutes.
2. Place pre-soaked nitrocellulose membrane into dot-blot apparatus, apply vacuum and seal apparatus by tightening screws.
3. Re-hydrate nitrocellulose by adding 100 μL of TBS to each well. Briefly apply vacuum but DO NOT completely dry the wells.
4. Confirm flow valve/vacuum chamber of the dot-blot apparatus is open to air and fill wells with 100 μL of a 0.5 ng/μL solution of either MEK1 or MEK2 target protein for a final assay amount of 50 ng of target protein per well.
5. Allow the target protein to filter through the membrane by gravity flow for 40 minutes at room temperature before drawing the remaining liquid through the membrane by vacuum filtration.
6. Block wells by adding 300 μL of 5% non-fat dried milk in TBS for 1 hour at room temperature.
7. Carefully aspirate the 5% blocking solution from each well.
8. Wash each well once by adding 100 μL of TBS. Pull the TBS through the membrane by vacuum filtration.
9. Add 100 μL of a 0.1 ng/μL solution of each of the MEK inhibitor lysates to by tested to one well containing MEK1 protein and one well containing MEK2 protein for a final assay amount of 10 ng of inhibitor per well. Incubate inhibitor lysates with MEK1/2 target protein for 40 minutes at room temperature before drawing the remaining lysate through the membrane by vacuum filtration.
10. Wash each well by adding 100 μL 1% SDS in TBS. Pull the 1% SDS in TBS through the membrane by vacuum filtration. Repeat this wash step two additional times for a total of three washes.
11. Apply vacuum and mark the membrane with a pen or pencil (so that membrane can be re-aligned after removal from the apparatus).
12. Turn off vacuum and remove the membrane from the apparatus.
13. Place membrane in a Petri dish (or equivalent vessel) and wash with 1% SDS in TBS for 5 minutes with gentle agitation (add enough 1% SDS in TBS to cover the entire membrane). Repeat this wash step four additional times for a total of five washes.
14. Wash membrane once in TBS (as described in step 13) to remove excess SDS detergent from the membrane.
15. Return membrane to the dot-blot apparatus as described in step 2.
16. Add 100 μL of βeta-Glo beta-galactosidase substrate to each well and incubate for 30 minutes at room temperature.
17. Vacuum filter βeta-Glo substrate through the membrane, remove the membrane from the apparatus and expose the membrane for 15 minutes in the FluorChem imager set for chemiluminescent detection.

The materials used in this assay were:
1. Dot-blot apparatus (Bio-Rad or equivalent)
2. Tris (Sigma, #252859 or equivalent)
3. SDS (ICN #811034 or equivalent)
4. NaCl (EMD #7647-14-5 or equivalent)
5. βeta-Glo Assay Kit (Promega #E4740)
6. Mek1 (Cell Signaling #M02-10G-10 or equivalent)
7. Mek2 (Cell Signaling #M03-10G-10 or equivalent)
8. FluorChem imager (Alpha Innotech or equivalent)

The image data was then quantified using the following protocol:
1. Open the dot blot image in the software application, ImageJ.
2. Use the rectangular selection tool to outline the first row.
3. Select Mark First Lane in the Special menu.
4. Move the rectangular selection (by clicking inside it and dragging) and outline (using Mark Next Lane) each of the other lanes in succession.
5. Use Plot Lanes to generate the lane profile plots.
6. Use the line drawing tool to draw base lines and drop lines so that each peak defines a closed area as shown above.
7. Measure the areas of the peaks by clicking inside each one in succession with the wand tool.
8. The data file with the peak measurements (dot intensity values) can then be saved as an Microsoft excel file and normalized and graphed.

Figure 26:
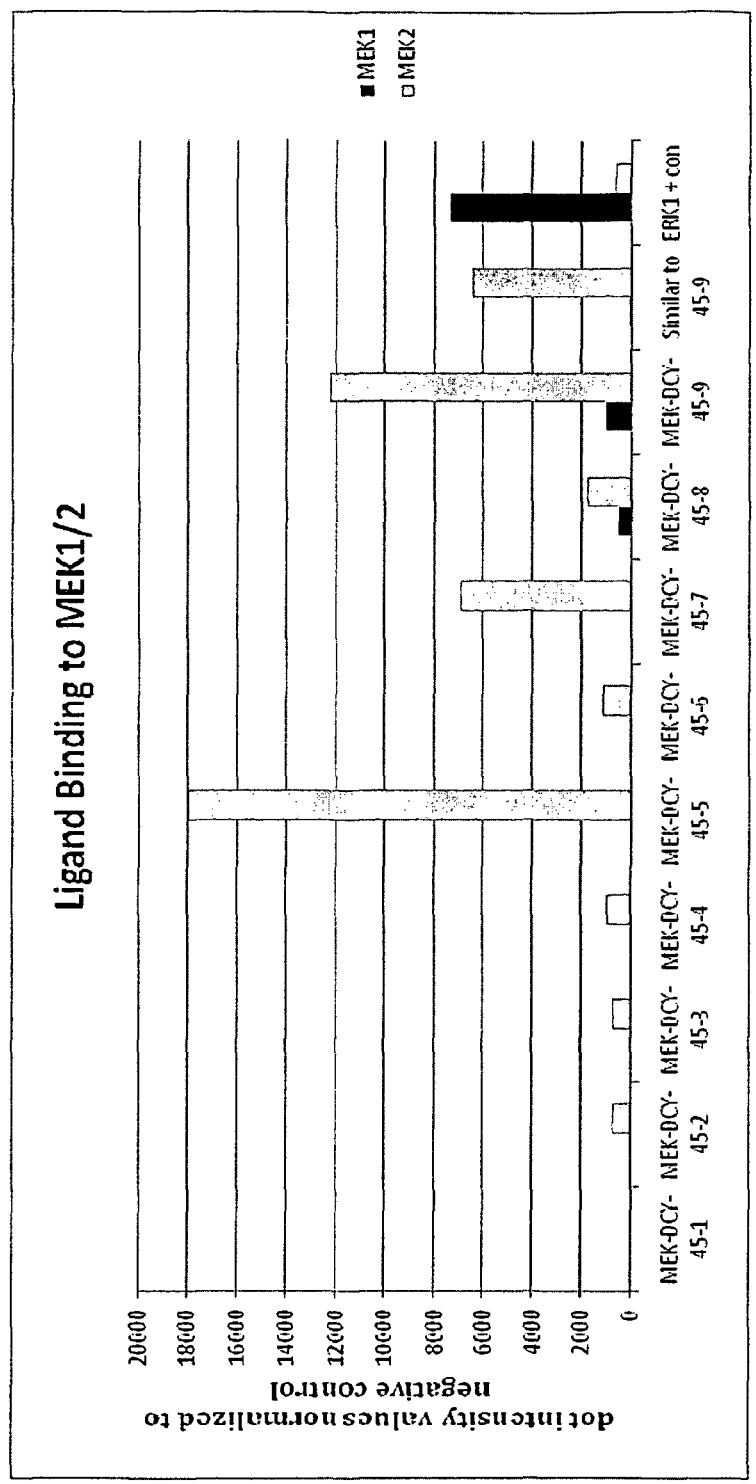
FIG. 26 shows the results of image analysis of protein dot blot binding assays of ligand-beta-galactosidase fusion proteins against MEK1 and MEK2 protein targets.

FIG. 26 represents the results of the image analysis of the protein dot blot binding assay, which shows that several of the fusion proteins exhibited binding activity against MEK1 and/or MEK 2.

Disclosed are ligands and polyligands that modulate MEK activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

What is claimed is:

1. A polynucleotide encoding a chimeric polypeptide polyligand comprising one or more copies of a polypeptide monomer selected from the group consisting of an amino acid sequence at least 80% identical to any one of SEQ ID NOS: 42, 46, 49, 50, or 51, wherein the polypeptide polyligand inhibits MEK activity.

2. The polynucleotide of claim 1, wherein the chimeric polypeptide polyligand is a polypeptide homopolyligand.

3. The polynucleotide of claim 1, wherein the chimeric polypeptide polyligand is a polypeptide heteropolyligand.

4. The polynucleotide of claim 1, wherein Xaa in any one of SEQ ID NOS: 42, 46, 49, 50, or 51, is any amino acid.

5. The polynucleotide of claim 1, wherein Xaa in any one of SEQ ID NOS: 42, 46, 49, 50, or 51, is an amino acid other than serine, tyrosine or threonine.

6. The polynucleotide of claim 1, wherein the chimeric polypeptide polyligand is linked to a subcellular localization signal, a reporter, and/or an epitope tag.

7. The polynucleotide of claim 1, wherein the chimeric polypeptide monomer is at least 85% identical to any one of SEQ ID NOS: 42, 46, 49, 50, or 51.

8. The polynucleotide of claim 1, wherein the chimeric polypeptide monomer is at least 90% identical to any one of SEQ ID NOS: 42, 46, 49, 50, or 51.

9. The polynucleotide of claim 1, wherein the chimeric polypeptide monomer is at least 95% identical to any one of SEQ ID NOS: 42, 46, 49, 50, or 51.

10. The polynucleotide of claim 1, wherein the chimeric polypeptide monomer is at least 96% identical to any one of SEQ ID NOS: 42, 46, 49, 50, or 51.

11. The polynucleotide of claim 1, wherein the chimeric polypeptide monomer is at least 97% identical to any one of SEQ ID NOS: 42, 46, 49, 50, or 51.

12. The polynucleotide of claim 1, wherein the chimeric polypeptide monomer is at least 98% identical to any one of SEQ ID NOS: 42, 46, 49, 50, or 51.

13. The polynucleotide of claim 1, wherein the chimeric polypeptide monomer is at least 99% identical to any one of SEQ ID NOS: 42, 46, 49, 50, or 51.

14. The polynucleotide of claim 1, wherein the chimeric polypeptide monomer is identical to one of SEQ ID NOS: 42, 46, 49, 50, or 51.

15. A vector comprising the polynucleotide of claim 1.

16. A host cell comprising the vector of claim 15.

17. A method of inhibiting MEK in a host cell, the method comprising transfecting the vector of claim 15 into a host cell, and culturing the host cell under conditions suitable to produce at least one copy of the chimeric polypeptide polyligand.

* * * * *

SEQUENCE LISTING

<160> NUMBER OF SEQ ID NOS: 55

<210> SEQ ID NO 1
<211> LENGTH: 91
<212> TYPE: PRT

<213> ORGANISM: artificial sequence
<220> FEATURE:
<223> OTHER INFORMATION: synthetic

<400> SEQUENCE: 1

Gly Val Ser Gly Gly Leu Ile Asp Ala Met Ala Asn Ala Phe Val Gly
1               5                   10                  15

Thr Arg Ser Tyr Met Ser Pro Gly Ala Ala Gly Arg Thr Pro Gly Arg
            20                  25                  30

Pro Leu Ala Ser Phe Gly Met Asp Ser Arg Pro Ala Gly Ala Tyr
        35                  40                  45

Cys Gln Arg Thr Leu Arg Glu Ile Gln Ile Leu Leu Arg Pro Gly Ala
    50                  55                  60

Ala Gly Asp His Thr Gly Phe Leu Ala Glu Phe Val Ala Thr Arg Trp
65                  70                  75                  80

Tyr Arg Ala Pro Glu Ile Met Leu Asn Ser Lys
                85                  90

<210> SEQ ID NO 2
<211> LENGTH: 273
<212> TYPE: DNA
<213> ORGANISM: artificial sequence
<220> FEATURE:
<223> OTHER INFORMATION: synthetic

<400> SEQUENCE: 2
ggcgtgagcg gcggcctgat cgacgccatg gccaacgcct tcgtgggcac caggagctac      60
atgagccccg cgccgccgg aaggaccccc ggcaggcccc tggccagctt cggcatggac     120
agcaggcccg ccggaggcgc ctactgccag aggaccctga gggagatcca gatcctgctg     180
aggcccggcg ccgccggaga ccacaccggc ttcctggccg agttcgtggc caccagatgg     240
tacagggccc ccgagatcat gctgaacagc aag                                  273

<210> SEQ ID NO 3
<211> LENGTH: 307
<212> TYPE: DNA
<213> ORGANISM: artificial sequence
<220> FEATURE:
<223> OTHER INFORMATION: synthetic

<400> SEQUENCE: 3
gctagcgccg gcggcgtgag cggcggcctg atcgacgcca tggccaacgc cttcgtgggc      60
accaggagct acatgagccc cggcgccgcc ggaaggaccc ccggcaggcc cctggccagc     120
ttcggcatgg acagcaggcc cgccggaggc gcctactgcc agaggaccct gagggagatc     180
cagatcctgc tgaggcccgg cgccgccgga gaccacaccg gcttcctggc cgagttcgtg     240
gccaccagat ggtacagggc ccccgagatc atgctgaaca gcaagcccgg gggaggcgga     300
atcgatt                                                               307

<210> SEQ ID NO 4
<211> LENGTH: 316
<212> TYPE: DNA
<213> ORGANISM: artificial sequence
<220> FEATURE:
<223> OTHER INFORMATION: synthetic

<400> SEQUENCE: 4
gctagcgcca ccatggccgg cggcgtgagc ggcggcctga tcgacgccat ggccaacgcc      60
ttcgtgggca ccaggagcta catgagcccc ggcgccgccg gaaggacccc cggcaggccc     120

```
ctggccagct tcggcatgga cagcaggccc gccggaggcg cctactgcca gaggaccctg      180
agggagatcc agatcctgct gaggcccggc gccgccggaa ccacaccgg cttcctggcc       240 gagttcgtgg ccaccagatg gtacagggcc cccgagatca tgctgaacag caagcccggg    300
ggaggcggaa tcgatt                                                      316
```

```
<210> SEQ ID NO 5
<211> LENGTH: 103
<212> TYPE: PRT
<213> ORGANISM: artificial sequence
<220> FEATURE:
<223> OTHER INFORMATION: synthetic

<400> SEQUENCE: 5
```

Thr Gly Phe Leu Ala Glu Phe Val Ala Thr Arg Trp Tyr Arg Ala Pro
1               5                   10                  15

Glu Ile Met Leu Asn Ser Lys Gly Pro Gly Ala Ala Gly Thr Gly Phe
            20                  25                  30

Leu Ala Glu Phe Val Ala Thr Arg Trp Tyr Arg Ala Pro Glu Ile Met
        35                  40                  45

Leu Asn Ser Lys Gly Pro Ala Gly Gly Ala Arg Thr Pro Gly Arg Pro
    50                  55                  60

Leu Ala Ser Phe Gly Met Asp Ser Arg Pro Gly Ala Ala Gly Asp His
65                  70                  75                  80

Thr Gly Phe Leu Ala Glu Phe Val Ala Thr Arg Trp Tyr Arg Ala Pro
                85                  90                  95

Glu Ile Met Leu Asn Ser Lys
            100

```
<210> SEQ ID NO 6
<211> LENGTH: 309
<212> TYPE: DNA
<213> ORGANISM: artificial sequence
<220> FEATURE:
<223> OTHER INFORMATION: synthetic

<400> SEQUENCE: 6
accggcttcc tggccgagtt cgtggccacc agatggtaca gggcccccga gatcatgctg     60
aacagcaagg ccccggcgc cgccggaacc ggcttcctgg ccgagttcgt ggccaccaga     120
tggtacaggg cccccgagat catgctgaac agcaagggcc ccgccggagg cgccaggacc    180
cccggcaggc ccctggccag cttcggcatg gacagcaggc ccggcgccgc cggagaccac    240
accggcttcc tggccgagtt cgtggccacc agatggtaca gggcccccga gatcatgctg    300
aacagcaag                                                            309
```

```
<210> SEQ ID NO 7
<211> LENGTH: 343
<212> TYPE: DNA
<213> ORGANISM: artificial sequence
<220> FEATURE:
<223> OTHER INFORMATION: synthetic

<400> SEQUENCE: 7
gctagcgccg gcaccggctt cctggccgag ttcgtggcca ccagatggta cagggccccc    60
gagatcatgc tgaacagcaa gggccccggc gccgccggaa ccggcttcct ggccgagttc    120
gtggccacca gatggtacag ggcccccgag atcatgctga acagcaaggg ccccgccgga    180
ggcgccagga ccccggcag gcccctggcc agcttcggca tggacagcag gcccggcgcc    240
```

```
gccggagacc acaccggctt cctggccgag ttcgtggcca ccagatggta cagggccccc      300
gagatcatgc tgaacagcaa gcccggggga ggcggaatcg att                       343

<210> SEQ ID NO 8
<211> LENGTH: 352
<212> TYPE: DNA
<213> ORGANISM: artificial sequence
<220> FEATURE:
<223> OTHER INFORMATION: synthetic

<400> SEQUENCE: 8
gctagcgcca ccatggccgg caccggcttc ctggccgagt tcgtggccac cagatggtac      60 agggccccg agatcatgct gaacagcaag ggccccggcg ccgccggaaa cggcttcctg      120
gccgagttcg tggccaccag atggtacagg gcccccgaga tcatgctgaa cagcaagggc      180
cccgccggag cgccaggac ccccggcagg ccctggcca gcttcggcat ggacagcagg       240 cccgcgccg ccggagacca caccggcttc ctggccgagt tcgtggccac cagatggtac      300 agggccccg agatcatgct gaacagcaag cccgggggag gcggaatcga tt              352

<210> SEQ ID NO 9
<211> LENGTH: 91
<212> TYPE: PRT
<213> ORGANISM: artificial sequence
<220> FEATURE:
<223> OTHER INFORMATION: synthetic

<400> SEQUENCE: 9

Gly Val Ser Gly Gly Leu Ile Asp Ser Met Ala Asn Ser Phe Val Gly
1               5                   10                  15

Thr Arg Ser Tyr Met Ser Pro Gly Ala Ala Gly Arg Thr Pro Gly Arg
            20                  25                  30

Pro Leu Ser Ser Tyr Gly Met Asp Ser Arg Pro Ala Gly Gly Ala Tyr
        35                  40                  45

Cys Gln Arg Thr Leu Arg Glu Ile Gln Ile Leu Leu Arg Pro Gly Ala
    50                  55                  60

Ala Gly Asp His Thr Gly Phe Leu Thr Glu Tyr Val Ala Thr Arg Trp
65                  70                  75                  80

Tyr Arg Ala Pro Glu Ile Met Leu Asn Ser Lys
            85                  90

<210> SEQ ID NO 10
<211> LENGTH: 273
<212> TYPE: DNA
<213> ORGANISM: artificial sequence
<220> FEATURE:
<223> OTHER INFORMATION: synthetic

<400> SEQUENCE: 10
ggcgtgagcg gcggcctgat cgacagcatg gccaacagct cgtgggcac caggagctac       60 atgagccccg gcgccgccgg aaggaccccc ggcaggcccc tgagcagcta cggcatggac     120
agcaggcccg ccggaggcgc ctactgccag aggaccctga gggagatcca gatcctgctg     180
aggcccggcg ccgccggaga ccacaccggc ttcctgaccg agtacgtggc caccagatgg     240
tacagggccc ccgagatcat gctgaacagc aag                                  273

<210> SEQ ID NO 11
<211> LENGTH: 307
<212> TYPE: DNA
```

```
<213> ORGANISM: artificial sequence
<220> FEATURE:
<223> OTHER INFORMATION: synthetic

<400> SEQUENCE: 11
gctagcgccg gcggcgtgag cggcggcctg atcgacagca tggccaacag cttcgtgggc    60
accaggagct acatgagccc cggcgccgcc ggaaggaccc ccggcaggcc cctgagcagc   120
tacggcatgg acagcaggcc cgccggaggc gcctactgcc agaggaccct gagggagatc   180
cagatcctgc tgaggcccgg cgccgccgga accacaccg gcttcctgac cgagtacgtg    240
gccaccagat ggtacagggc ccccgagatc atgctgaaca gcaagcccgg gggaggcgga   300
atcgatt                                                             307

<210> SEQ ID NO 12
<211> LENGTH: 316
<212> TYPE: DNA
<213> ORGANISM: artificial sequence
<220> FEATURE:
<223> OTHER INFORMATION: synthetic

<400> SEQUENCE: 12
gctagcgcca ccatggccgg cggcgtgagc ggcggcctga tcgacagcat ggccaacagc    60
ttcgtgggca ccaggagcta catgagcccc ggcgccgccg gaaggacccc cggcaggccc   120
ctgagcagct acggcatgga cagcaggccc gccggaggcg cctactgcca gaggaccctg   180
agggagatcc agatcctgct gaggcccggc gccgccggag accacaccgg cttcctgacc   240
gagtacgtgg ccaccagatg gtacagggcc cccgagatca tgctgaacag caagcccggg   300
ggaggcggaa tcgatt                                                   316

<210> SEQ ID NO 13
<211> LENGTH: 103
<212> TYPE: PRT
<213> ORGANISM: artificial sequence
<220> FEATURE:
<223> OTHER INFORMATION: synthetic

<400> SEQUENCE: 13

Thr Gly Phe Leu Thr Glu Tyr Val Ala Thr Arg Trp Tyr Arg Ala Pro
1               5                   10                  15

Glu Ile Met Leu Asn Ser Lys Gly Pro Gly Ala Ala Gly Thr Gly Phe
            20                  25                  30

Leu Thr Glu Tyr Val Ala Thr Arg Trp Tyr Arg Ala Pro Glu Ile Met
        35                  40                  45

Leu Asn Ser Lys Gly Pro Ala Gly Gly Ala Arg Thr Pro Gly Arg Pro
    50                  55                  60

Leu Ser Ser Tyr Gly Met Asp Ser Arg Pro Ala Ala Gly Asp His
65                  70                  75                  80

Thr Gly Phe Leu Thr Glu Tyr Val Ala Thr Arg Trp Tyr Arg Ala Pro
                85                  90                  95

Glu Ile Met Leu Asn Ser Lys
            100

<210> SEQ ID NO 14
<211> LENGTH: 309
<212> TYPE: DNA
<213> ORGANISM: artificial sequence
<220> FEATURE:
<223> OTHER INFORMATION: synthetic
```

```
<400> SEQUENCE: 14
accggcttcc tgaccgagta cgtggccacc agatggtaca gggcccccga gatcatgctg      60
aacagcaagg gccccggcgc cgccggaacc ggcttcctga ccgagtacgt ggccaccaga     120
tggtacaggg cccccgagat catgctgaac agcaagggcc ccgccggagg cgccaggacc     180
cccggcaggc ccctgagcag ctacggcatg acagcaggc ccggcgccgc cggagaccac      240
accggcttcc tgaccgagta cgtggccacc agatggtaca gggcccccga gatcatgctg     300
aacagcaag                                                             309

<210> SEQ ID NO 15
<211> LENGTH: 343
<212> TYPE: DNA
<213> ORGANISM: artificial sequence
<220> FEATURE:
<223> OTHER INFORMATION: synthetic

<400> SEQUENCE: 15
gctagcgccg gcaccggctt cctgaccgag tacgtggcca ccagatggta cagggccccc      60
gagatcatgc tgaacagcaa gggccccggc gccgccggaa ccggcttcct gaccgagtac     120
gtggccacca gatggtacag gggccccgag atcatgctga acagcaaggg ccccgccgga     180
ggcgccagga ccccggcag gccctgagc agctacggca tggacagcag gcccggcgcc      240 gccgagacc acaccggctt cctgaccgag tacgtggcca ccagatggta cagggccccc      300
gagatcatgc tgaacagcaa gcccggggga ggcggaatcg att                       343

<210> SEQ ID NO 16
<211> LENGTH: 352
<212> TYPE: DNA
<213> ORGANISM: artificial sequence
<220> FEATURE:
<223> OTHER INFORMATION: synthetic

<400> SEQUENCE: 16
gctagcgcca ccatggccgg caccggcttc ctgaccgagt acgtggccac cagatggtac      60
agggcccccg agatcatgct gaacagcaag ggccccggcg ccgccggaac cggcttcctg     120
accgagtacg tggccaccag atggtacagg gccccgaga tcatgctgaa cagcaagggc      180
cccgccggag cgccaggac cccggcagg ccctgagca gctacggcat ggacagcagg        240
cccggcgccg ccggagacca caccggcttc ctgaccgagt acgtggccac cagatggtac     300
agggcccccg agatcatgct gaacagcaag cccgggggag cggaatcga tt              352

<210> SEQ ID NO 17
<211> LENGTH: 100
<212> TYPE: PRT
<213> ORGANISM: artificial sequence
<220> FEATURE:
<223> OTHER INFORMATION: synthetic

<400> SEQUENCE: 17

Phe Asp Gly Ile Trp Lys Ala Ser Phe Thr Thr Phe Thr Val Thr Lys
1               5                   10                  15

Tyr Trp Phe Tyr Arg Pro Gly Ala Ala Gly Asp His Thr Gly Phe Leu
            20                  25                  30

Ala Glu Phe Val Ala Thr Arg Trp Tyr Arg Ala Pro Glu Ile Met Leu
        35                  40                  45

Asn Ser Lys Pro Ala Gly Gly Ala Arg Thr Pro Gly Arg Pro Leu Ala
    50                  55                  60
```

Ser Phe Gly Met Asp Ser Arg Pro Gly Ala Ala Gly Thr Gly Phe Leu
65                  70                  75                  80

Ala Glu Phe Val Ala Thr Arg Trp Tyr Arg Ala Pro Glu Ile Met Leu
                85                  90                  95

Asn Ser Lys Gly
            100

<210> SEQ ID NO 18
<211> LENGTH: 300
<212> TYPE: DNA
<213> ORGANISM: artificial sequence
<220> FEATURE:
<223> OTHER INFORMATION: synthetic

<400> SEQUENCE: 18
ttcgacggca tctggaaggc cagcttcacc accttcaccg tgaccaagta ctggttctac      60
aggcccggcg ccgccggaga ccacaccggc ttcctggccg agttcgtggc caccagatgg     120
tacagggccc ccgagatcat gctgaacagc aagcccgccg gaggcgccag gaccccnggc    180
aggcccctgg ccagcttcgg catggacagc aggcccggcg ccgccggaac cggcttcctg     240
gccgagttcg tggccaccag atggtacagg gccccgaga tcatgctgaa cagcaagggc     300

<210> SEQ ID NO 19
<211> LENGTH: 334
<212> TYPE: DNA
<213> ORGANISM: artificial sequence
<220> FEATURE:
<223> OTHER INFORMATION: synthetic

<400> SEQUENCE: 19
gctagcgccg gcttcgacgg catctggaag gccagcttca ccaccttcac cgtgaccaag      60
tactggttct acaggcccgg cgccgccgga gaccacaccg gcttcctggc cgagttcgtg     120
gccaccagat ggtacagggc ccccgagatc atgctgaaca gcaagcccgc cggaggcgcc     180 aggaccccg gcaggcccct ggccagcttc ggcatggaca gcaggcccgg cgccgccgga     240
accggcttcc tggccgagtt cgtggccacc agatggtaca gggcccccga gatcatgctg     300
aacagcaagg gccccggggg aggcggaatc gatt                                 334

<210> SEQ ID NO 20
<211> LENGTH: 343
<212> TYPE: DNA
<213> ORGANISM: artificial sequence
<220> FEATURE:
<223> OTHER INFORMATION: synthetic

<400> SEQUENCE: 20
gctagcgcca ccatggccgg cttcgacggc atctggaagg ccagcttcac caccttcacc      60
gtgaccaagt actggttcta caggcccggc gccgccggag accacaccgg cttcctggcc     120
gagttcgtgg ccaccagatg gtacagggcc cccgagatca tgctgaacag caagcccgcc     180
ggaggcgcca ggaccccgg caggcccctg gccagcttcg gcatggacag caggcccggc     240
gccgccggaa ccggcttcct ggccgagttc gtggccacca gatggtacag ggcccccgag     300
atcatgctga acagcaaggg ccccgggga ggcggaatcg att                        343

<210> SEQ ID NO 21
<211> LENGTH: 127
<212> TYPE: PRT
<213> ORGANISM: artificial sequence
<220> FEATURE:
<223> OTHER INFORMATION: synthetic

<400> SEQUENCE: 21

```
Ile Cys Asp Phe Gly Leu Ala Arg Val Ala Asp Pro Asp His Asp His
1               5                   10                  15

Thr Gly Phe Leu Ala Glu Phe Val Ala Thr Arg Trp Tyr Arg Ala Pro
            20                  25                  30

Glu Ile Met Leu Asn Ser Lys Pro Gly Ala Ala Gly Ile Cys Asp Phe
        35                  40                  45

Gly Leu Ala Arg Val Ala Asp Pro Asp His Asp His Thr Gly Phe Leu
    50                  55                  60

Ala Glu Phe Val Ala Thr Arg Trp Tyr Arg Ala Pro Glu Ile Met Leu
65                  70                  75                  80

Asn Ser Lys Pro Gly Ala Ala Gly Ile Cys Asp Phe Gly Leu Ala Arg
                85                  90                  95

Val Ala Asp Pro Asp His Asp His Thr Gly Phe Leu Ala Glu Phe Val
            100                 105                 110

Ala Thr Arg Trp Tyr Arg Ala Pro Glu Ile Met Leu Asn Ser Lys
        115                 120                 125
```

<210> SEQ ID NO 22
<211> LENGTH: 381
<212> TYPE: DNA
<213> ORGANISM: artificial sequence
<220> FEATURE:
<223> OTHER INFORMATION: synthetic

<400> SEQUENCE: 22

```
atctgcgact tcggcctggc cagggtcgcc gaccccgacc acgaccacac cggcttcctg      60
gccgagttcg tggccaccag atggtacagg gcccccgaga tcatgctgaa cagcaagccc     120
ggcgccgccg gaatctgcga cttcggcctg gccagggtcg ccgaccccga ccacgaccac     180
accggcttcc tggccgagtt cgtggccacc agatggtaca gggcccccga gatcatgctg     240
aacagcaagc ccggcgccgc cggaatctgc gacttcggcc tggccagggt cgccgacccc     300
gaccacgacc acaccggctt cctggccgag ttcgtggcca ccagatggta cagggccccc     360
gagatcatgc tgaacagcaa g                                                381
```

<210> SEQ ID NO 23
<211> LENGTH: 415
<212> TYPE: DNA
<213> ORGANISM: artificial sequence
<220> FEATURE:
<223> OTHER INFORMATION: synthetic

<400> SEQUENCE: 23

```
gctagcgccg gcatctgcga cttcggcctg gccagggtcg ccgaccccga ccacgaccac      60
accggcttcc tggccgagtt cgtggccacc agatggtaca gggcccccga gatcatgctg     120
aacagcaagc ccggcgccgc cggaatctgc gacttcggcc tggccagggt cgccgacccc     180
gaccacgacc acaccggctt cctggccgag ttcgtggcca ccagatggta cagggccccc     240
gagatcatgc tgaacagcaa gcccggcgcc gccggaatct gcgacttcgg cctggccagg     300
gtcgccgacc ccgaccacga ccacaccggc ttcctggccg agttcgtggc caccagatgg     360
tacagggccc ccgagatcat gctgaacagc aagcccgggg aggcggaat cgatt          415
```

<210> SEQ ID NO 24

<211> LENGTH: 424
<212> TYPE: DNA
<213> ORGANISM: artificial sequence
<220> FEATURE:
<223> OTHER INFORMATION: synthetic

<400> SEQUENCE: 24

| | |
|---|---|
| gctagcgcca ccatggccgg catctgcgac ttcggcctgg ccagggtcgc cgaccccgac | 60 |
| cacgaccaca ccggcttcct ggccgagttc gtggccacca gatggtacag gccccccgag | 120 |
| atcatgctga acagcaagcc cggcgccgcc ggaatctgcg acttcggcct ggccagggtc | 180 |
| gccgaccccg accacgacca caccggcttc ctggccgagt cgtggccac cagatggtac | 240 |
| agggcccccg agatcatgct gaacagcaag cccggcgccg ccggaatctg cgacttcggc | 300 |
| ctggccaggg tcgccgaccc cgaccacgac acaccggct tcctggccga gttcgtggcc | 360 |
| accagatggt acagggcccc cgagatcatg ctgaacagca gcccgggggg aggcggaatc | 420 |
| gatt | 424 |

<210> SEQ ID NO 25
<211> LENGTH: 174
<212> TYPE: PRT
<213> ORGANISM: artificial sequence
<220> FEATURE:
<223> OTHER INFORMATION: synthetic

<400> SEQUENCE: 25

Tyr Cys Gln Arg Thr Leu Arg Glu Ile Lys Ile Leu Leu Arg Phe Arg
1               5                   10                  15

His Glu Asn Ile Ile Gly Ile Asn Asp Ile Ile Arg Ala Pro Thr Ile
            20                  25                  30

Glu Gln Met Lys Asp Val Tyr Ile Val Gln Asp Leu Met Glu Thr Asp
        35                  40                  45

Leu Tyr Lys Leu Leu Lys Thr Gln His Leu Ser Asn Asp His Ile Cys
    50                  55                  60

Tyr Phe Leu Tyr Gln Ile Leu Arg Gly Leu Lys Tyr Ile His Ser Ala
65                  70                  75                  80

Asn Val Leu His Arg Asp Leu Lys Pro Ser Asn Leu Leu Leu Asn Thr
                85                  90                  95

Thr Cys Asp Leu Lys Ile Cys Asp Phe Gly Leu Ala Arg Val Ala Asp
            100                 105                 110

Pro Asp His Asp His Thr Gly Phe Leu Ala Glu Phe Val Ala Thr Arg
        115                 120                 125

Trp Tyr Arg Ala Pro Glu Ile Met Leu Asn Ser Lys Gly Tyr Thr Lys
    130                 135                 140

Ser Ile Asp Ile Trp Ser Val Gly Cys Ile Leu Ala Glu Met Leu Ser
145                 150                 155                 160

Asn Arg Pro Ile Phe Pro Gly Lys His Tyr Leu Asp Gln Leu
                165                 170

<210> SEQ ID NO 26
<211> LENGTH: 522
<212> TYPE: DNA
<213> ORGANISM: artificial sequence
<220> FEATURE:
<223> OTHER INFORMATION: synthetic

<400> SEQUENCE: 26

| | |
|---|---|
| tactgccaga ggaccctgag ggagatcaag atcctgctga ggttcaggca cgagaacatc | 60 |

```
atcggcatca acgacatcat cagggccccc accatcgagc agatgaagga cgtgtacatc    120
gtgcaggacc tgatggagac cgacctgtac aagctgctga agacccagca cctgagcaac    180
gaccacatct gctacttcct gtaccagatc ctgaggggcc tgaagtacat ccacagcgcc    240
aacgtgctgc acagggacct gaagcccagc aacctcctgc tgaacaccac ctgtgacctg    300
aagatttgcg acttcggcct ggccagggtc gccgaccccg accacgacca caccggcttc    360
ctggccgagt tcgtggccac cagatggtac agggcccccg agatcatgct gaacagcaag    420
ggctacacca agagcatcga catctggagc gtgggctgca tcctggccga gatgctgagc    480
aacaggccca tcttccccgg caagcactac ctggaccagc tg                      522

<210> SEQ ID NO 27
<211> LENGTH: 556
<212> TYPE: DNA
<213> ORGANISM: artificial sequence
<220> FEATURE:
<223> OTHER INFORMATION: synthetic

<400> SEQUENCE: 27
gctagcgccg gctactgcca gaggaccctg agggagatca agatcctgct gaggttcagg    60
cacgagaaca tcatcggcat caacgacatc atcagggccc ccaccatcga gcagatgaag    120
gacgtgtaca tcgtgcagga cctgatggag accgacctgt acaagctgct gaagacccag    180
cacctgagca acgaccacat ctgctacttc ctgtaccaga tcctgagggg cctgaagtac    240
atccacagcg ccaacgtgct gcacagggac ctgaagccca gcaacctcct gctgaacacc    300
acctgtgacc tgaagatttg cgacttcggc ctggccaggg tcgccgaccc cgaccacgac    360
cacaccggct cctggccga gttcgtggcc accagatggt acagggcccc cgagatcatg    420
ctgaacagca agggctacac caagagcatc gacatctgga gcgtgggctg catcctggcc    480
gagatgctga gcaacaggcc catcttcccc ggcaagcact acctggacca gctgcccggg    540
ggaggcggaa tcgatt                                                   556

<210> SEQ ID NO 28
<211> LENGTH: 565
<212> TYPE: DNA
<213> ORGANISM: artificial sequence
<220> FEATURE:
<223> OTHER INFORMATION: synthetic

<400> SEQUENCE: 28
gctagcgcca ccatggccgg ctactgccag aggaccctga gggagatcaa gatcctgctg    60
aggttcaggc acgagaacat catcggcatc aacgacatca tcagggcccc caccatcgag    120
cagatgaagg acgtgtacat cgtgcaggac ctgatggaga ccgacctgta caagctgctg    180
aagacccagc acctgagcaa cgaccacatc tgctacttcc tgtaccagat cctgagggc    240 ctgaagtaca tccacagcgc caacgtgctg cacagggacc tgaagcccag caacctcctg    300
ctgaacacca cctgtgacct gaagatttgc gacttcggcc tggccagggt cgccgacccc    360
gaccacgacc acaccggctt cctggccgag ttcgtggcca ccagatggta cagggccccc    420
gagatcatgc tgaacagcaa gggctacacc aagagcatcg acatctggag cgtgggctgc    480
atcctggccg agatgctgag caacaggccc atcttccccg gcaagcacta cctggaccag    540
ctgcccgggg gaggcggaat cgatt                                         565

<210> SEQ ID NO 29
<211> LENGTH: 145
```

```
<212> TYPE: PRT
<213> ORGANISM: artificial sequence
<220> FEATURE:
<223> OTHER INFORMATION: synthetic

<400> SEQUENCE: 29
```

Glu His Gln Thr Tyr Cys Gln Arg Thr Leu Arg Glu Ile Gln Ile Leu
1               5                   10                  15

Leu Arg Phe Arg His Glu Asn Val Ile Gly Ile Arg Asp Ile Leu Arg
            20                  25                  30

Ala Ser Thr Leu Glu Ala Met Arg Asp Val Tyr Ile Val Gln Asp Leu
        35                  40                  45

Met Glu Thr Asp Leu Tyr Lys Leu Leu Lys Ser Gln Gln Leu Ser Asn
    50                  55                  60

Asp His Ile Cys Tyr Phe Leu Tyr Gln Ile Leu Arg Gly Leu Lys Tyr
65                  70                  75                  80

Ile His Ser Ala Asn Val Leu His Arg Asp Leu Lys Pro Ser Asn Leu
                85                  90                  95

Leu Ile Asn Thr Thr Cys Asp Leu Lys Ile Cys Asp Phe Gly Leu Ala
            100                 105                 110

Arg Ile Ala Asp Pro Glu His Asp His Thr Gly Phe Leu Ala Glu Ala
        115                 120                 125

Val Ala Thr Arg Trp Tyr Arg Ala Pro Glu Ile Met Leu Asn Ser Lys
    130                 135                 140

Gly
145

```
<210> SEQ ID NO 30
<211> LENGTH: 435
<212> TYPE: DNA
<213> ORGANISM: artificial sequence
<220> FEATURE:
<223> OTHER INFORMATION: synthetic

<400> SEQUENCE: 30
gagcaccaga cctactgcca gaggaccctg agggagatcc agatcctgct gaggttcagg      60
cacgagaacg tgatcggcat cagggacatc ctgagggcca gcaccctcga agccatgagg     120
gacgtgtaca tcgtgcagga cctgatggag accgacctgt acaagctgct gaaaagccag     180
cagctgagca cgaccacat ctgctacttc ctgtaccaga tcctgagggg cctgaagtac      240
atccacagcg ccaacgtgct gcacagggac ctgaagccca gcaacctcct gatcaacacc     300
acctgtgacc tgaagatttg cgacttcggc ctggccagga tcgccgaccc cgagcacgac     360
cacaccggct tcctggccga ggccgtggcc accagatggt acagggcccc cgagatcatg     420
ctgaacagca agggc                                                      435

<210> SEQ ID NO 31
<211> LENGTH: 469
<212> TYPE: DNA
<213> ORGANISM: artificial sequence
<220> FEATURE:
<223> OTHER INFORMATION: synthetic

<400> SEQUENCE: 31
gctagcgccg cgagcacca gacctactgc cagaggaccc tgagggagat ccagatcctg       60
ctgaggttca ggcacgagaa cgtgatcggc atcagggaca tcctgagggc cagcaccctc     120
gaagccatga gggacgtgta catcgtgcag gacctgatgg agaccgacct gtacaagctg     180
```

| | |
|---|---|
| ctgaaaagcc agcagctgag caacgaccac atctgctact tcctgtacca gatcctgagg | 240 |
| ggcctgaagt acatccacag cgccaacgtg ctgcacaggg acctgaagcc cagcaacctc | 300 |
| ctgatcaaca ccacctgtga cctgaagatt tgcgacttcg gcctggccag gatcgccgac | 360 |
| cccgagcacg accacaccgg cttcctggcc gaggccgtgg ccaccagatg gtacagggcc | 420 |
| cccgagatca tgctgaacag caagggcccc ggggaggcg gaatcgatt | 469 |

<210> SEQ ID NO 32
<211> LENGTH: 478
<212> TYPE: DNA
<213> ORGANISM: artificial sequence
<220> FEATURE:
<223> OTHER INFORMATION: synthetic

<400> SEQUENCE: 32

| | |
|---|---|
| gctagcgcca ccatggccgg cgagcaccag acctactgcc agaggaccct gagggagatc | 60 |
| cagatcctgc tgaggttcag cacgagaac gtgatcggca tcaggacat cctgagggcc | 120 |
| agcaccctcg aagccatgag ggacgtgtac atcgtgcagg acctgatgga gaccgacctg | 180 |
| tacaagctgc tgaaaagcca gcagctgagc aacgaccaca tctgctactt cctgtaccag | 240 |
| atcctgaggg gcctgaagta catccacagc gccaacgtgc tgcacaggga cctgaagccc | 300 |
| agcaacctcc tgatcaacac cacctgtgac ctgaagattt gcgacttcgg cctggccagg | 360 |
| atcgccgacc ccgagcacga ccacaccggc ttcctggccg aggccgtggc caccagatgg | 420 |
| tacagggccc ccgagatcat gctgaacagc aagggccccg ggggaggcgg aatcgatt | 478 |

<210> SEQ ID NO 33
<211> LENGTH: 84
<212> TYPE: PRT
<213> ORGANISM: artificial sequence
<220> FEATURE:
<223> OTHER INFORMATION: synthetic

<400> SEQUENCE: 33

Ala Asp Pro Asp His Asp His Thr Gly Phe Leu Ala Glu Ala Val Ala
1               5                   10                  15
Thr Arg Trp Arg Arg Pro Ala Ala Ala Tyr Cys Gln Arg Thr Leu Arg
            20                  25                  30
Glu Ile Gln Ile Leu Leu Arg Phe Pro Gly Gly Gly Ala Asp Pro Asp
        35                  40                  45
His Asp His Thr Gly Phe Leu Ala Glu Ala Val Ala Thr Arg Trp Arg
    50                  55                  60
Arg Pro Ala Ala Ala Tyr Cys Gln Arg Thr Leu Arg Glu Ile Gln Ile
65                  70                  75                  80
Leu Leu Arg Phe

<210> SEQ ID NO 34
<211> LENGTH: 252
<212> TYPE: DNA
<213> ORGANISM: artificial sequence
<220> FEATURE:
<223> OTHER INFORMATION: synthetic

<400> SEQUENCE: 34

| | |
|---|---|
| gccgaccccg accacgacca caccggcttc ctggccgagg ccgtggccac cagatggagg | 60 |
| aggcccgccg ccgcctactg ccagaggacc ctgagggaga tccagatcct gctgaggttc | 120 |
| cccggcggcg gcgccgaccc cgaccacgac cacaccggct tcctggccga ggccgtggcc | 180 |

```
accagatgga ggaggcccgc cgccgcctac tgccagagga ccctgaggga gatccagatc    240
ctgctgaggt tc                                                       252
```

<210> SEQ ID NO 35
<211> LENGTH: 286
<212> TYPE: DNA
<213> ORGANISM: artificial sequence
<220> FEATURE:
<223> OTHER INFORMATION: synthetic

<400> SEQUENCE: 35

```
gctagcgccg cgccgacccc cgaccacgac cacaccggct tcctggccga ggccgtggcc    60
accagatgga ggaggcccgc cgccgcctac tgccagagga ccctgaggga gatccagatc    120
ctgctgaggt tccccggcgg cggcgccgac cccgaccacg accacaccgg cttcctggcc    180
gaggccgtgg ccaccagatg gaggaggccc gccgccgcct actgccagag gaccctgagg    240
gagatccaga tcctgctgag gttccccggg ggaggcggaa tcgatt                  286
```

<210> SEQ ID NO 36
<211> LENGTH: 295
<212> TYPE: DNA
<213> ORGANISM: artificial sequence
<220> FEATURE:
<223> OTHER INFORMATION: synthetic

<400> SEQUENCE: 36

```
gctagcgcca ccatggccgg cgccgacccc gaccacgacc acaccggctt cctggccgag    60
gccgtggcca ccagatggag gaggcccgcc gccgcctact gccagaggac cctgagggag    120
atccagatcc tgctgaggtt ccccggcggc ggcgccgacc ccgaccacga ccacaccggc    180
ttcctggccg aggccgtggc caccagatgg aggaggcccg ccgccgccta ctgccagagg    240
accctgaggg agatccagat cctgctgagg ttccccgggg gaggcggaat cgatt        295
```

<210> SEQ ID NO 37
<211> LENGTH: 393
<212> TYPE: PRT
<213> ORGANISM: human
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (298)..(298)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid

<400> SEQUENCE: 37

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60
```

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Xaa Met Ala Asn Xaa Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Xaa Ser Xaa Gly Met Asp Ser
290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390

<210> SEQ ID NO 38
<211> LENGTH: 379
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid

<400> SEQUENCE: 38

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
                35                  40                  45

Gly Glu Gly Ala Tyr Gly Met Val Ser Ser Ala Tyr Asp His Val Arg
            50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
                100                 105                 110

Glu Ala Met Arg Asp Val Tyr Ile Val Gln Asp Leu Met Glu Thr Asp
            115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Xaa Glu Xaa Val Ala Thr Arg
            195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Glu Pro Phe Thr Phe Ala Met Glu Leu
            340                 345                 350

Asp Asp Leu Pro Lys Glu Arg Leu Lys Glu Leu Ile Phe Gln Glu Thr
355                 360                 365

Ala Arg Phe Gln Pro Gly Val Leu Glu Ala Pro
            370                 375

<210> SEQ ID NO 39
<211> LENGTH: 360
<212> TYPE: PRT

```
<213> ORGANISM: human
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid

<400> SEQUENCE: 39
```

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
            20                  25                  30

Glu Gly Ala Tyr Gly Met Val Cys Ser Ala Tyr Asp Asn Val Asn Lys
        35                  40                  45

Val Arg Val Ala Ile Lys Lys Ile Ser Pro Phe Glu His Gln Thr Tyr
    50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Xaa Glu Xaa Val Ala Thr Arg Trp
            180                 185                 190

Tyr Arg Ala Pro Glu Ile Met Leu Asn Ser Lys Gly Tyr Thr Lys Ser
        195                 200                 205

Ile Asp Ile Trp Ser Val Gly Cys Ile Leu Ala Glu Met Leu Ser Asn
210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser

<210> SEQ ID NO 40
<211> LENGTH: 178
<212> TYPE: PRT
<213> ORGANISM: human

<400> SEQUENCE: 40

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 41
<211> LENGTH: 22
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 41

Gly Val Ser Gly Gly Leu Ile Asp Xaa Met Ala Asn Xaa Phe Val Gly
1               5                   10                  15

Thr Arg Ser Tyr Met Ser
            20

<210> SEQ ID NO 42
<211> LENGTH: 15
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (8)..(8)

<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 42

Arg Thr Pro Gly Arg Pro Leu Xaa Ser Xaa Gly Met Asp Ser Arg
1               5                   10                  15

<210> SEQ ID NO 43
<211> LENGTH: 25
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 43

Asp His Thr Gly Phe Leu Xaa Glu Xaa Val Ala Thr Arg Trp Tyr Arg
1               5                   10                  15

Ala Pro Glu Ile Met Leu Asn Ser Lys
            20                  25

<210> SEQ ID NO 44
<211> LENGTH: 24
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 44

Thr Gly Phe Leu Xaa Glu Xaa Val Ala Thr Arg Trp Tyr Arg Ala Pro
1               5                   10                  15

Glu Ile Met Leu Asn Ser Lys Gly
            20

<210> SEQ ID NO 45
<211> LENGTH: 39
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 45

Ile Cys Asp Phe Gly Leu Ala Arg Val Ala Asp Pro Asp His Asp His
1               5                   10                  15

-continued

```
Thr Gly Phe Leu Xaa Glu Xaa Val Ala Thr Arg Trp Tyr Arg Ala Pro
            20              25                  30

Glu Ile Met Leu Asn Ser Lys
        35
```

```
<210> SEQ ID NO 46
<211> LENGTH: 174
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid

<400> SEQUENCE: 46

Tyr Cys Gln Arg Thr Leu Arg Glu Ile Lys Ile Leu Leu Arg Phe Arg
1               5                   10                  15

His Glu Asn Ile Ile Gly Ile Asn Asp Ile Ile Arg Ala Pro Thr Ile
            20                  25                  30

Glu Gln Met Lys Asp Val Tyr Ile Val Gln Asp Leu Met Glu Thr Asp
        35                  40                  45

Leu Tyr Lys Leu Leu Lys Thr Gln His Leu Ser Asn Asp His Ile Cys
    50                  55                  60

Tyr Phe Leu Tyr Gln Ile Leu Arg Gly Leu Lys Tyr Ile His Ser Ala
65                  70                  75                  80

Asn Val Leu His Arg Asp Leu Lys Pro Ser Asn Leu Leu Leu Asn Thr
                85                  90                  95

Thr Cys Asp Leu Lys Ile Cys Asp Phe Gly Leu Ala Arg Val Ala Asp
            100                 105                 110

Pro Asp His Asp His Thr Gly Phe Leu Xaa Glu Xaa Val Ala Thr Arg
        115                 120                 125

Trp Tyr Arg Ala Pro Glu Ile Met Leu Asn Ser Lys Gly Tyr Thr Lys
    130                 135                 140

Ser Ile Asp Ile Trp Ser Val Gly Cys Ile Leu Ala Glu Met Leu Ser
145                 150                 155                 160

Asn Arg Pro Ile Phe Pro Gly Lys His Tyr Leu Asp Gln Leu
                165                 170
```

```
<210> SEQ ID NO 47
<211> LENGTH: 145
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid

<400> SEQUENCE: 47

Glu His Gln Thr Tyr Cys Gln Arg Thr Leu Arg Glu Ile Gln Ile Leu
1               5                   10                  15
```

```
Leu Arg Phe Arg His Glu Asn Val Ile Gly Ile Arg Asp Ile Leu Arg
             20                  25                  30

Ala Ser Thr Leu Glu Ala Met Arg Asp Val Tyr Ile Val Gln Asp Leu
         35                  40                  45

Met Glu Thr Asp Leu Tyr Lys Leu Leu Lys Ser Gln Gln Leu Ser Asn
 50                  55                  60

Asp His Ile Cys Tyr Phe Leu Tyr Gln Ile Leu Arg Gly Leu Lys Tyr
65                  70                  75                  80

Ile His Ser Ala Asn Val Leu His Arg Asp Leu Lys Pro Ser Asn Leu
             85                  90                  95

Leu Ile Asn Thr Thr Cys Asp Leu Lys Ile Cys Asp Phe Gly Leu Ala
        100                 105                 110

Arg Ile Ala Asp Pro Glu His Asp His Thr Gly Phe Leu Xaa Glu Xaa
    115                 120                 125

Val Ala Thr Arg Trp Tyr Arg Ala Pro Glu Ile Met Leu Asn Ser Lys
    130                 135                 140

Gly
145

<210> SEQ ID NO 48
<211> LENGTH: 19
<212> TYPE: PRT
<213> ORGANISM: artificial sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 48

Ala Asp Pro Asp His Asp His Thr Gly Phe Leu Xaa Glu Xaa Val Ala
1               5                  10                  15

Thr Arg Trp

<210> SEQ ID NO 49
<211> LENGTH: 14
<212> TYPE: PRT
<213> ORGANISM: artificial sequence
<220> FEATURE:
<223> OTHER INFORMATION: synthetic

<400> SEQUENCE: 49

Tyr Cys Gln Arg Thr Leu Arg Glu Ile Gln Ile Leu Leu Arg
1               5                  10

<210> SEQ ID NO 50
<211> LENGTH: 15
<212> TYPE: PRT
<213> ORGANISM: artificial sequence
<220> FEATURE:
<223> OTHER INFORMATION: synthetic

<400> SEQUENCE: 50

Tyr Cys Gln Arg Thr Leu Arg Glu Ile Gln Ile Leu Leu Arg Phe
1               5                  10                  15

<210> SEQ ID NO 51
<211> LENGTH: 21
```

```
<212> TYPE: PRT
<213> ORGANISM: artificial sequence
<220> FEATURE:
<223> OTHER INFORMATION: synthetic

<400> SEQUENCE: 51

Phe Asp Gly Ile Trp Lys Ala Ser Phe Thr Thr Phe Thr Val Thr Lys
1               5                   10                  15

Tyr Trp Phe Tyr Arg
            20

<210> SEQ ID NO 52
<211> LENGTH: 5
<212> TYPE: PRT
<213> ORGANISM: Artificial Sequence
<220> FEATURE:
<223> OTHER INFORMATION: spacer

<400> SEQUENCE: 52

Pro Gly Ala Ala Gly
1               5

<210> SEQ ID NO 53
<211> LENGTH: 6
<212> TYPE: PRT
<213> ORGANISM: Artificial Sequence
<220> FEATURE:
<223> OTHER INFORMATION: spacer

<400> SEQUENCE: 53

Arg Arg Pro Ala Ala Ala
1               5

<210> SEQ ID NO 54
<211> LENGTH: 5
<212> TYPE: PRT
<213> ORGANISM: Artificial Sequence
<220> FEATURE:
<223> OTHER INFORMATION: spacer

<400> SEQUENCE: 54

Pro Ala Gly Gly Ala
1               5

<210> SEQ ID NO 55
<211> LENGTH: 4
<212> TYPE: PRT
<213> ORGANISM: Artificial Sequence
<220> FEATURE:
<223> OTHER INFORMATION: spacer

<400> SEQUENCE: 55

Pro Gly Gly Gly
1
```